United States Patent
Campbell et al.

(10) Patent No.: US 10,262,555 B2
(45) Date of Patent: Apr. 16, 2019

(54) FACILITATING AWARENESS AND CONVERSATION THROUGHPUT IN AN AUGMENTATIVE AND ALTERNATIVE COMMUNICATION SYSTEM

(71) Applicant: Microsoft Technology Licensing, LLC, Redmond, WA (US)

(72) Inventors: Jon Campbell, Redmond, WA (US); Ann Paradiso, Shoreline, WA (US); Jay Beavers, Duvall, WA (US); Mira E. Shah, Seattle, WA (US); Meredith Morris, Bellevue, WA (US); Alexander Fiannaca, Seattle, WA (US); Harish Kulkarni, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 599 days.

(21) Appl. No.: 14/880,061

(22) Filed: Oct. 9, 2015

(65) Prior Publication Data
US 2017/0103679 A1 Apr. 13, 2017

(51) Int. Cl.
*G10L 15/22* (2006.01)
*G09B 21/00* (2006.01)
(Continued)

(52) U.S. Cl.
CPC ........... *G09B 21/00* (2013.01); *A61F 4/00* (2013.01); *G06F 3/00* (2013.01); *G06F 3/167* (2013.01);
(Continued)

(58) Field of Classification Search
None
See application file for complete search history.

(56) References Cited

U.S. PATENT DOCUMENTS

| 5,481,622 A | 1/1996 | Gerhardt et al. |
| 6,157,403 A | 12/2000 | Nagata |

(Continued)

FOREIGN PATENT DOCUMENTS

| CN | 102131157 A | 7/2011 |
| EP | 0702355 B1 | 1/2002 |

(Continued)

OTHER PUBLICATIONS

"What are the Different Page Roles and What can they do", Facebook, Oct. 16, 2014, https://www.facebook.com/help/289207354498410.
(Continued)

*Primary Examiner* — Abul K Azad
(74) *Attorney, Agent, or Firm* — Alleman Hall Creasman & Tuttle LLP

(57) ABSTRACT

Speech generating devices, communication systems, and methods for communicating using the devices and systems are disclosed herein. In certain examples, a communication system is configured to receive a generated communication, establish a connection between a speech generating device and a computing device subsequent to receipt of the generated communication, and transmit the generated communication to the computing device. In other examples, a computing device is configured to establish a connection with a speech generating device, and receive a transmission generated by the speech generating device following the connection, the transmission including previously generated communications or real-time communication segments or proxies. In other examples, a speech generating device is configured to establish a connection with one or more computing devices, receive one or more suggestions from at least one computing device during generation of the communication, and display a suggestion on the display device as a shortcut input key.

17 Claims, 12 Drawing Sheets

(51) Int. Cl.
*G10L 13/02* (2013.01)
*G06F 3/16* (2006.01)
*G06F 17/27* (2006.01)
*G10L 13/00* (2006.01)
*A61F 4/00* (2006.01)
*G06F 3/00* (2006.01)
*G06F 17/30* (2006.01)

(52) U.S. Cl.
CPC ...... *G06F 17/276* (2013.01); *G06F 17/30654* (2013.01); *G10L 13/00* (2013.01); *G10L 13/02* (2013.01); *G10L 15/22* (2013.01)

(56) References Cited

U.S. PATENT DOCUMENTS

| | | | |
|---|---|---|---|
| 6,163,281 | A | 12/2000 | Torch |
| 6,192,396 | B1 | 2/2001 | Kohler |
| 6,775,359 | B1 | 8/2004 | Ron et al. |
| 6,785,649 | B1 | 8/2004 | Hoory et al. |
| 6,868,383 | B1 | 3/2005 | Bangalore et al. |
| 6,988,068 | B2 | 1/2006 | Fado et al. |
| 6,993,474 | B2 | 1/2006 | Curry et al. |
| 7,165,033 | B1 | 1/2007 | Liberman |
| 7,224,774 | B1 | 5/2007 | Brown et al. |
| 7,254,709 | B1 | 8/2007 | Richard |
| 7,461,352 | B2 | 12/2008 | Katsuranis |
| 7,679,534 | B2 | 3/2010 | Kay et al. |
| 7,774,202 | B2 | 8/2010 | Spengler et al. |
| 8,004,398 | B2 | 8/2011 | Chriss |
| 8,224,652 | B2 | 7/2012 | Wang et al. |
| 8,275,110 | B2 | 9/2012 | Vendrow |
| 8,285,552 | B2 | 10/2012 | Wang et al. |
| 8,386,255 | B2 | 2/2013 | Michaelis |
| 8,463,594 | B2 | 6/2013 | Au |
| 8,515,763 | B2 | 8/2013 | Dong et al. |
| 8,538,402 | B2 | 9/2013 | Vidal et al. |
| 8,655,661 | B2 | 2/2014 | Hymel et al. |
| 8,706,827 | B1 * | 4/2014 | Noble .................. G10L 13/027 704/9 |
| 8,854,447 | B2 | 10/2014 | Conness et al. |
| 8,914,014 | B2 | 12/2014 | Vidal et al. |
| 8,914,290 | B2 | 12/2014 | Hendrickson et al. |
| 8,986,218 | B2 | 3/2015 | De Lemos et al. |
| 8,989,713 | B2 | 3/2015 | Doulton |
| 9,443,518 | B1 | 9/2016 | Gauci |
| 9,560,206 | B2 | 1/2017 | Jones et al. |
| 9,830,477 | B2 | 11/2017 | Bhogal et al. |
| 2002/0085030 | A1 | 7/2002 | Ghani |
| 2003/0058267 | A1 | 3/2003 | Warren |
| 2003/0061208 | A1 | 3/2003 | Ohashi |
| 2004/0078445 | A1 | 4/2004 | Malik |
| 2005/0062726 | A1 * | 3/2005 | Marsden .............. G06F 1/1626 345/173 |
| 2005/0175218 | A1 | 8/2005 | Vertegaal et al. |
| 2006/0110008 | A1 | 5/2006 | Vertegaal et al. |
| 2006/0206310 | A1 | 9/2006 | Ravikumar et al. |
| 2007/0002130 | A1 | 1/2007 | Hartkop |
| 2007/0016426 | A1 | 1/2007 | Hershey et al. |
| 2007/0055520 | A1 | 3/2007 | Mowatt et al. |
| 2007/0066916 | A1 | 3/2007 | Lemos |
| 2007/0081090 | A1 | 4/2007 | Singh |
| 2007/0288242 | A1 | 12/2007 | Spengler et al. |
| 2008/0065468 | A1 | 3/2008 | Berg et al. |
| 2008/0096533 | A1 | 4/2008 | Manfredi et al. |
| 2008/0154601 | A1 | 6/2008 | Stifelman et al. |
| 2009/0012793 | A1 | 1/2009 | Dao et al. |
| 2009/0040289 | A1 | 2/2009 | Hetherington et al. |
| 2009/0070205 | A1 | 3/2009 | Altberg et al. |
| 2009/0210795 | A1 | 8/2009 | Katsuranis |
| 2009/0310762 | A1 | 12/2009 | Velius |
| 2009/0315827 | A1 | 12/2009 | Elvesjo et al. |
| 2010/0174586 | A1 | 7/2010 | Berg, Jr. et al. |
| 2010/0199340 | A1 | 8/2010 | Jonas et al. |
| 2010/0222098 | A1 | 9/2010 | Garg |
| 2011/0098056 | A1 | 4/2011 | Rhoads et al. |
| 2011/0115798 | A1 | 5/2011 | Nayar et al. |
| 2011/0125503 | A1 | 5/2011 | Dong et al. |
| 2011/0173214 | A1 | 7/2011 | Karim |
| 2011/0173705 | A1 | 7/2011 | Sundaram et al. |
| 2011/0191699 | A1 | 8/2011 | Cunningham et al. |
| 2011/0276396 | A1 | 11/2011 | Rathod |
| 2012/0004511 | A1 | 1/2012 | Sivadas |
| 2012/0105486 | A1 | 5/2012 | Lankford et al. |
| 2012/0109835 | A1 | 5/2012 | Barefoot et al. |
| 2012/0110096 | A1 | 5/2012 | Smarr et al. |
| 2012/0137254 | A1 | 5/2012 | Cunningham et al. |
| 2012/0179972 | A1 | 7/2012 | Hacid et al. |
| 2012/0209654 | A1 | 8/2012 | Romagnino et al. |
| 2012/0221639 | A1 | 8/2012 | Mallet et al. |
| 2012/0259925 | A1 | 10/2012 | Braudes |
| 2012/0324491 | A1 | 12/2012 | Bathiche et al. |
| 2013/0054244 | A1 | 2/2013 | Bao et al. |
| 2013/0065204 | A1 | 3/2013 | LoStracco et al. |
| 2013/0079061 | A1 | 3/2013 | Jadhav et al. |
| 2013/0091223 | A1 | 4/2013 | DeLuca et al. |
| 2013/0100025 | A1 | 4/2013 | Vernacchia |
| 2013/0159426 | A1 | 6/2013 | Milic-Frayling et al. |
| 2013/0205408 | A1 | 8/2013 | Yerli |
| 2013/0210406 | A1 | 8/2013 | Vidal et al. |
| 2013/0262119 | A1 | 10/2013 | Latorre-Martinez et al. |
| 2013/0281079 | A1 | 10/2013 | Vidal et al. |
| 2013/0304829 | A1 | 11/2013 | Olsen et al. |
| 2013/0307997 | A1 | 11/2013 | O'keefe et al. |
| 2013/0316746 | A1 | 11/2013 | Miller et al. |
| 2014/0019542 | A1 | 1/2014 | Rao et al. |
| 2014/0053228 | A1 | 2/2014 | Mahadevan et al. |
| 2014/0090091 | A1 | 3/2014 | Prakash et al. |
| 2014/0093848 | A1 | 4/2014 | Ashbrook |
| 2014/0115068 | A1 | 4/2014 | Kurupacheril et al. |
| 2014/0149884 | A1 | 5/2014 | Flynn et al. |
| 2014/0176813 | A1 | 6/2014 | Conness et al. |
| 2014/0195918 | A1 | 7/2014 | Friedlander |
| 2014/0253458 | A1 | 9/2014 | Patel |
| 2014/0280206 | A1 | 9/2014 | Krishnamurthy et al. |
| 2014/0280603 | A1 | 9/2014 | Rideout et al. |
| 2014/0280605 | A1 | 9/2014 | Zhang |
| 2014/0317660 | A1 | 10/2014 | Cheung et al. |
| 2014/0317760 | A1 | 10/2014 | Gold et al. |
| 2015/0019216 | A1 | 1/2015 | Singh et al. |
| 2015/0031416 | A1 | 1/2015 | Labowicz et al. |
| 2015/0039584 | A1 | 2/2015 | Bastide et al. |
| 2015/0121227 | A1 | 4/2015 | Peng et al. |
| 2015/0121256 | A1 | 4/2015 | Kim |
| 2015/0195313 | A1 | 7/2015 | Lewis et al. |
| 2015/0213214 | A1 | 7/2015 | Patak et al. |
| 2015/0234939 | A1 | 8/2015 | Aharony et al. |
| 2015/0244669 | A1 | 8/2015 | Ying |
| 2015/0347774 | A1 | 12/2015 | Krstic et al. |
| 2016/0014059 | A1 | 1/2016 | Rathod |
| 2016/0036962 | A1 | 2/2016 | Rand |
| 2016/0063276 | A1 | 3/2016 | Pycock |
| 2016/0086179 | A1 | 3/2016 | Barbier |
| 2016/0134580 | A1 | 5/2016 | Castera et al. |
| 2016/0140671 | A1 | 5/2016 | Hong |
| 2016/0219057 | A1 | 7/2016 | Das et al. |
| 2016/0275952 | A1 | 9/2016 | Kashtan et al. |
| 2017/0147795 | A1 | 5/2017 | Sardesai et al. |
| 2018/0039511 | A1 | 2/2018 | Nakano et al. |

FOREIGN PATENT DOCUMENTS

| | | |
|---|---|---|
| EP | 2426902 A1 | 3/2012 |
| WO | 2011088053 A2 | 7/2011 |
| WO | 2014178044 A1 | 11/2014 |
| WO | 2014193824 A1 | 12/2014 |

OTHER PUBLICATIONS

"APPCrawler", Published on: Nov. 3, 2014, retrieved Sep. 14, 2015; Available at: http://apperawlr.com/ipad/verbally.

(56) References Cited

OTHER PUBLICATIONS

"Compusult", Published on: Mar. 10, 2011, Available at: http://www.compusult.at/at-website/our-products/outspoken-communicator-mobile.
"DynaVox V™ and Vmax™", Retrieved on: Aug. 17, 2015, Available at: https://www.google.co.in/url?sa=t&rct=j&q=&esrc=s&source=web&cd=3&cad=rja&uact=8&ved=0CCoQFjACahUKEwj5hYyz47HHAhUSBY4KHVq-Awo&url=http%3A%2F%2Fuk.dynavoxtech.com%2Fdownload.ashx%3FFileId%3D1870%26DocId%3D66b36cc2-21b1-470f-a782-808f65c81567&ei=HrLSVfn-lpKKuATa_I5Q&usg=AFQjCNGs5OgYMPQv3PkU3X_P33O80ph8Ng&bvm=bv.99804247,d.c2E.
"Mobile Devices & Communication Apps: An AAC-RERC White Paper", In White Paper of AAC-RERC, Mar. 14, 2011, 8 pages.
"MyTalkTools Mobile", Retrieved on: Sep. 7, 2015, Available at: https://itunes.apple.com/us/app/mytalktools-mobile/id324286288?mt=8.
"Neurotiq_Sensoree", Published on: Mar. 5, 2014, Available at: http://sensoree.com/artifacts/neurotiq/.
"Onevoice", Published on: Jan. 17, 2012; Available at: http://onevoiceapp.com/features/.
"ReadItToMe—Unique Handsfree", Retrieved on: Aug. 17, 2015, Available at: https://play.google.com/store/apps/details?id=robj.readit.tomefree&hl=en.
"Rehabilitation Engineering Research Center on Augmentative and Alternative Communication", Retrieved on: Sep. 7, 2015, Available at: https://rerc-aac.psu.edu/development/d3-developing-a-smart-predictor-app-for-aac-conversation/.
"Text Message Reader", Published on: Jun. 30, 2015, Available at: https://play.google.com/store/apps/details?id=com.allaboutee.textmessagereader.
"Tobii C12—AAC Device for Independence", Retrieved on: Sep. 7, 2015, Available at: http://www.tobii.com/en/assistive-technology/global/products/old-or-discontinued-products/tobii-c12/.
"Tobii Dynavox Compass", Retrieved on: Sep. 7, 2015, Available at: https://itunes.apple.com/us/app/tobii-dynavox-compass/id907329432?mt=8.
"User Agent Accessibility Guidelines 1.0", In Technical Report of W3C Candidate Recommendation, Sep. 12, 2001, 38 pages.
Andreas Paepcke et al., "EchoTree: Engaged Conversation when Capabilities are Limited", In Technical Report of Stanford InfoLab, Sep. 11, 2015, pp. 1-5.
Arce, Nicole, "Twitch Introduces Whisper Feature: Here's How to Use the Private Messaging System", Published on: Jun. 11, 2015, Available at: http://www.techtimes.com/articles/59663/20150611/twitch-introduces-whisper-feature-heres-how-to-use-the-private-messaging-system.htm.
Barnes, et al., "A Framework for Centralized Conferencing", Published on: Jun. 2008, Available at: https://tools.ietf.org/html/rfc5239.
Brian Roark et al., "Towards Technology-Assisted Co-Construction with Communication Partners", In Proceedings of the 2nd Workshop on Speech and Language Processing for Assistive Technologies, Jul. 30, 2011, pp. 22-31.
Calliou, et al., "Supporting People who use AAC Strategies: in the Home, School & Community", Published on: Feb. 2008, Available at: http://www.setbc.org/Download/LearningCentre/Communication/AAC_Guide_V4_Revise_2008.pdf.
Isidoros Perikos et al., "Recognizing Emotion Presence in Natural Language Sentences", In Proceedings of 14th International Conference on Engineering Applications of Neural Networks, Sep. 13, 2014, 10 pages.
Jakobs, Thomas, "Co-Construction for AAC Devices", Retrieved on: Sep. 7, 2015, Available at: http://grantome.com/grant/NIH/R43-DC014294-01.
John L. Arnott et al., "Towards the Improvement of Augmentative and Alternative Communication through the Modelling of Conversation", Computer and Speech Language, Sep. 2013, pp. 1194-1211, vol. 27, No. 6.
Kieron Monks, "Feeling Glum, Happy, Aroused? New Technology Can Detect Your Mood", Published on Feb. 4, 2014, 10 pages, Available at: http://edition.cnn.com/2014/02/04/tech/innovation/this-new-tech-can-detect-your-mood/.
Linda J. Burkhart et al., "Partner-Assisted Communication Strategies for Children Who Face Multiple Challenges", Proceedings of 17th International Symposium on Algorithms and Computation, Dec. 18, 2006, 35 pages.
Luis Filipe Garcia et al., "Measuring the Performance of a Location-Aware Text Prediction System", In Journal of ACM Transactions on Accessible Computing, Jun. 2015, 29 pages, vol. 7, Issue 1.
Meder, Allison, "Mobile Media Devices and Communication Applications as a Form of Augmentative and Alternative Communication: An Assessment of Family Wants, Needs, and Preferences", In Master Thesis of Arts, Mar. 28, 2012, 79 pages.
P.M. Chavan et al., "Real Time Emotion Recognition through Facial Expressions for Desktop Devices", International Journal of Emerging Science and Engineering, May 2013, pp. 104-108, vol. 1, Issue 7.
Park, Donggyu, "Trytalk at School", Retrieved on: Sep. 7, 2015, Available at: https://itunes.apple.com/us/app/trytalk-at-school/id583216304?mt=8.
Shaun K. Kane, "What We Talk About: Designing a Context-Aware Communication Tool for People with Aphasia", In Proceedings of the 14th international ACM SIGACCESS conference on Computers and accessibility, Oct. 22, 2012, pp. 49-56.
Xu Zhe et al., "Text-to-Emotion Engine for Real Time Internet Communication", In Proceedings of International Symposium on Communication Systems, Networks, and DSPs, Jul. 2002, 5 pages.
Yong, Sarah, "Mobile Apps as Tools for Augmentative and Alternative Communication", Published on: Oct. 31, 2014; Available at: Http://Www.Iacentre.Org.Sg/Inclusivetech/Mobile-Apps-As-Tools-For-Augmentative-And-Alternative-Communication.
Fleishman, Glenn, "Use Chat Services for Remote Access", Retrieved From <<https://www.macworld.com/article/1152708/remoteaccesschat.html>>, Jul. 20, 2010, 7 pages.
"How Does Messaging Work in Whatsapp? Is This the Right Approach for Communication Between Client and Server? Is the Client Always Connected to the Internet when Waiting for a Response?", Retrieved From<<https://www.quora.com/How-does-messaging-work-in-WhatsApp-Is-this-the-right-approach-for-communication-between-client-and-server-Is-the-client-always-connected-to-the-internet-when-waiting-for-a-response>>, May 25, 2014, 5 Pages.
"Second Written Opinion Issued in PCT Application No. PCT/US2016/052374", dated Sep. 18, 2017, 7 Pages.
"International Preliminary Report on Patentability Issued in PCT Application No. PCT/US2016/052374", dated Jan. 9, 2018, 8 Pages.
"International Search Report & Written Opinion Issued in PCT Application No. PCT/US2016/052374", dated Dec. 12, 2016, 14 Pages.
"Non Final Office Action Issued in U.S. Appl. No. 14/880,092", dated Oct. 6, 2016, 36 Pages.
"Notice of Allowance Issued in U.S. Appl. No. 14/880,092", dated Feb. 22, 2017, 11 Pages.
"Non Final Office Action Issued in U.S. Appl. No. 14/880,127", dated Sep. 28, 2016, 29 Pages.
"Non Final Rejection Issued in U.S. Appl. No. 14/880,127", dated May 11, 2017, 31 Pages.
"Notice of Allowance Issued in U.S. Appl. No. 14/880,127", dated May 2, 2018, 11 Pages.
Filho, et al., "Enabling Continuous Emotional Status Display in Mobile Text Chat", In Springer Publication—Network and Parallel Computing, Jul. 19, 2015, 9 Pages.
"International Search Report and Written Opinion Issued in PCT Application No. PCT/US2016/052372", dated Dec. 6, 2016, 11 Pages.
"Second Written Opinion Issued in PCT Application No. PCT/US2016/052372", dated Sep. 18, 2017, 6 Pages.
"International Search Report and Written Opinion Issued in PCT Application No. PCT/US2016/052373", dated Dec. 8, 2016, 12 Pages.

(56) References Cited

OTHER PUBLICATIONS

"Second Written Opinion Issued in PCT Application No. PCT/US2016/052373", dated Sep. 13, 2017, 7 Pages.

* cited by examiner

FACILITATING AWARENESS AND CONVERSATION THROUGHPUT IN AN AUGMENTATIVE AND ALTERNATIVE COMMUNICATION SYSTEM

BACKGROUND

Many people with physical or cognitive challenges (e.g., severe speech impairments) may use Augmentative and Alternative Communication (AAC) systems in order to express themselves. This may include individuals who suffer from autism, amyotrophic lateral sclerosis (ALS), brain injuries, or strokes.

Certain AAC systems include speech generating devices. A speech generating device (SGD) acts as a proxy for conveying speech to those nearby as a prosthetic for a loss of speech.

Certain SGDs may include an electronic interface with specialized software configured to assist the user in creating a message that may be translated into an electronic voice output. SGDs may produce the electronic voice output by using digitized recordings of natural speech or through speech synthesis.

There are several challenges in communicating with a speech generating device. One challenge is that the SGD may have a very slow conversational throughput rate, with users generally producing only 8-10 words per minute. As such, there may be "dead time" during a conversation when the SGD user is inputting text into their device. In some instances, this slow communication pace may prompt a conversation partner to attempt to finish the SGD user's sentences for them, look over their shoulder as they input characters or words into their device, or ask a second question before the user has finished preparing a response to the first question. Such interaction may be undesired by the SGD user.

Another challenge with a speech generating device is that the electronic voice output of the SGD may not convey adequate emotion for the user. In other words, while the electronic voice output may be more "natural" in terms of sounding more like a human rather than prototypical "machine" speech, the output generally lacks emotive aspects of speech critical to communication.

Furthermore, an additional challenge with certain speech generating devices is being able to direct the inputted text to a distinct conversation partner. Certain SGDs only provide for broadcasting the inputted text at a predefined volume to nearby individuals around the user of the SGD.

Various workarounds to these challenges include using text messaging or email, or using something other than the SGD (e.g., eyebrow movements) to communicate the information or indicate the need for a more private conversation. This can be problematic because a caregiver may not be nearby, thus there is no ability to signal the caregiver. Texting or email are non-ideal because they require too many additional actions by the user, such as switching to a very different portion of the SGD software interface, selecting the recipient, and so on. Further, not all SGDs support email or text.

SUMMARY

Communication systems, speech generating devices (SGDs), and methods of using communication systems and SGDs are described herein. In one or more embodiments, a communication system is provided. The system includes a server configured to wirelessly communicate with a speech generating device and a computing device over a communication network, wherein the server is configured to: (1) receive a generated communication from the speech generating device, (2) establish a connection between the speech generating device and the computing device subsequent to receipt of the generated communication, and (3) transmit the generated communication to the computing device.

In another embodiment, a computing device is provided. The computing device includes at least one processor, and at least one memory coupled to the at least one processor, the at least one memory including computer program code for one or more programs; the at least one memory and the computer program code configured to, with the at least one processor, cause the computing device to: establish a connection with a speech generating device via a communication network and receive a transmission generated by the speech generating device, wherein the transmission comprises at least one of: (1) a previously generated communication, (2) a segment of a communication being generated in real-time, (3) a social cue proxy of the real-time communication, or (4) an emotional proxy of the previously generated communication or the real-time communication.

In another embodiment, a speech generating device is provided. The speech generating device includes a display device and an input device configured to generate a communication to be displayed on the display device. The speech generating device further includes at least one processor coupled to the display device and input device, wherein the speech generating device, with the at least one processor, is configured to (1) establish a connection with one or more computing devices via a communication network, (2) receive one or more suggestions from at least one computing device during generation of the communication, and (3) display at least one suggestion on the display device as a shortcut input key.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWING FIGURES

For a more complete understanding of the disclosure, reference is made to the following detailed description and accompanying drawing figures, in which like reference numerals may be used to identify like elements in the figures.

Figure 1:
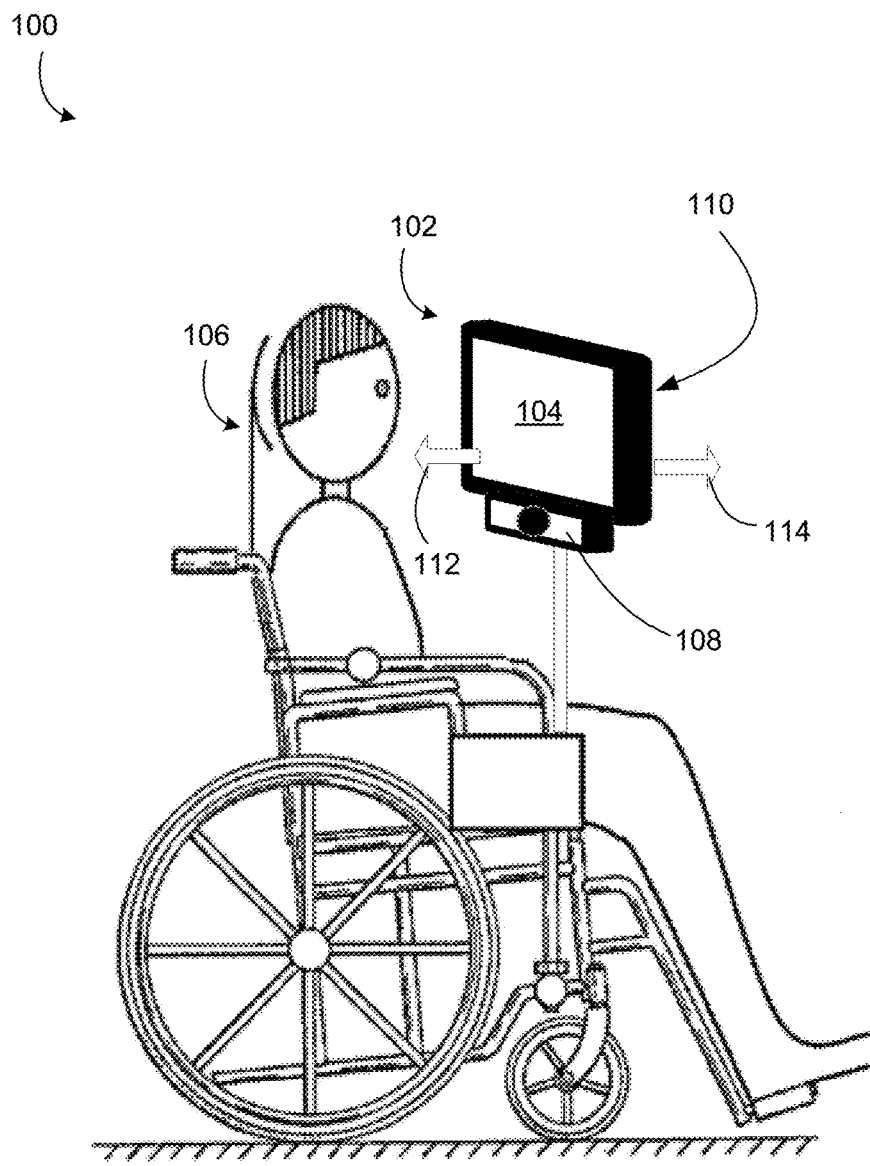
FIG. 1 depicts an example of a communication system having a speech generating device.
Figure 1:
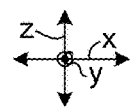

While the disclosed devices, systems, and methods are representative of embodiments in various forms, specific embodiments are illustrated in the drawings (and are hereafter described), with the understanding that the disclosure is intended to be illustrative, and is not intended to limit the claim scope to the specific embodiments described and illustrated herein.

DETAILED DESCRIPTION

Disclosed herein are speech generating devices (SGD), augmentative and alternative communication (AAC) systems, and methods for communicating using a SGD or AAC system. Such devices, systems, or methods have several potential end-uses or applications, including improving communication between a SGD user and a conversation partner, as well as preserving the autonomy of the SGD user.

For example, the devices and systems described herein may address slow communication pace through use of social cue proxies. In certain examples, a user of a SGD may provide a social cue proxy (1) indicating that the user is typing or composing a message, (2) indicating that the user is speaking or about to speak, (3) indicating that the user is requesting to speak, (4) requesting assistance, (5) identifying an emergency, (6) indicating that the user is calibrating the input device of the SGD (e.g., calibrating the eye gaze tracking device), (7) indicating that the SGD is idle.

Additionally, or alternatively, emotional proxies may be provided with the SGD user's communication output (e.g., electronic voice output). The user may identify an emotion with the communication by selecting an emotion from a chart, emoji, image, graphic, or avatar on a display of the SGD. In other examples, emotion may be inferred by the SGD analyzing the user's communication message. The selected or inferred emotion may be translated into an emotional proxy and displayed on a display device for the conversation partner to see.

Further, in certain examples, the SGD user may direct the communication message (and, e.g., the emotional or social cue proxy associated with the communication message) toward a distinct conversation partner or group of conversation partners. The SGD user may also control the level of sharing for the communication message for various groups or circles of conversation partners as the SGD user is compositing the message.

In additional examples, one or more conversation partners may discreetly assist the SGD user in developing the user's message. This assistance may take place using a connected computing device that is part of the communication system, wherein the computing device is separate from the SGD device. The computing device (e.g., smartphone, tablet, laptop computer) may be connected through use of a software application installed on the computing device (e.g., computer program code), wherein the application on the computing device is configured to communicate through a communication network (e.g., via a server) with the speech generating software application installed and operating on the SGD.

As used herein, the term "speech generating device" may refer to an electronic communication device wherein text and/or multimedia are selected by a user to create a message or communication, and the message is relayed to a conversation partner. The message may be relayed aurally, visually, or both. In some examples, the SGD is used by an individual as a primary method of communication due to a severe speech impairment. Nonetheless, use of the SGD is not limited to individuals suffering from speech impairments.

As used herein, the term "user" or "communicator" may refer to the individual generating the communication message using the speech generating device.

As used herein, the term "conversation partner," "receiver," or "recipient" may refer to the individual or group of individuals receiving a communication from the user or assisting the user in generating a message. A conversation partner may receive a communication from a SGD user by listening to audio output from the SGD or a separate computing device, or by viewing a display screen of the SGD or a display screen of a separate computing device connected with the speech generating device within a communication system or communication network.

As used herein, the term "connected" may refer to a computing device or display device that is in communication with the SGD via a communication network. The communication network may include wired networks, wireless networks, or combinations thereof. The communication network may include a server configured to receive and transmit signals from the computing devices and speech generating devices. A wireless network may be a cellular telephone network, an 802.11, 802.16, 802.20, or WiMax network. Further, the network may be a public network, such as the Internet, a private network, such as an intranet, or combinations thereof, and may utilize a variety of networking protocols now available or later developed including, but not limited to TCP/IP based networking protocols.

Speech Generating Devices and Communication Systems

FIG. 1 depicts a non-limiting a communication system 100 including a speech generating device (SGD) 102. The SGD 102 includes a first display device 104 configured to be positioned in front of or face a user 106 of the SGD 102. The communication system 100 further includes an input device 108 configured to generate a communication on the first display device 104. The communication system 100 may further include one or more speakers to play the generated communication. In certain examples, the input device 108 and speakers are part of the SGD 102.

The input device 108 may be an eye gaze tracking device; a pointing device such as a stylus, mouse, or joystick; a keyboard; an audio input device; a video input device; a haptic input device; or a device for receiving wired or wireless data transmissions. In certain examples, the input device 108 is an eye gaze tracking device. The eye gaze tracking device may work in communication with the first display device 104, where text and/or multimedia (e.g., images, audio, video) displayed on the first display device 104 are selected by the user 106 through interaction with the eye gaze tracking device. In other words, the user 106 may select text and/or multimedia displayed on the first display device 104 using the eye gaze tracking device to generate a communication, which is also displayed on the first display device. Additionally, the eye gaze tracking device may be able to monitor whether or not the eyes of the SGD user 106 are closed for at least a certain amount of time, which may provide an indication if the SGD user 106 is sleeping.

The SGD 102 may further include one or more cameras configured to take pictures or video in the direction of the SGD user 106 or in the opposing direction away from the user 106. A camera positioned in the direction of the user 106 may be configured to monitor the eyes of the user 106 to determine if the user is awake or sleeping. The SGD 102 may further include a processor and/or speech generating software (e.g., computer program code) configured to analyze input from the input device to generate a message. Additional components of the SGD 102 are described in detail below in the section "Exemplary Computing Environment."

The communication system 100 or SGD 102 may further include a second display device 110. In certain examples, the second display device 110 is physically connected to or part of the SGD 102. In other examples, the second display device is part of the communication system 100 and is separate from and wirelessly in communication with the SGD 102.

The second display device 110 may be positioned in a separate direction from the first display device 104. For example, the first display device 104 may be positioned with a display screen projecting in a first direction 112 (e.g., toward the user 106), and the second display device 110 may have a screen or display projecting in a second direction 114 different from the first direction 112 (e.g., at an angle greater than 0° from the first direction, at an angle between 90° and 270° from the first direction). In one example, the second display device 110 is positioned on the opposite side of the SGD 102 such that the second display device 110 is positioned in a direction 114 at an angle 180° from the first direction 112.

The second display device and positioning of the second display device are advantageous in addressing certain challenges in communications between a user of a speech generating device and a conversation partner. For example, the second display device may identify a social cue or emotion of the SGD user to the conversation partner, provide an avenue for discreet communication between the SGD user and conversation partner, and/or allow the conversation partner to unobtrusively assist in constructing the SGD user's communication message. Further discussion regarding social cue and emotional proxies, avenues for discreet communications using a SGD, and avenues for interaction with the SGD user during generation of the communication message are provided in greater detail below.

Figure 2:
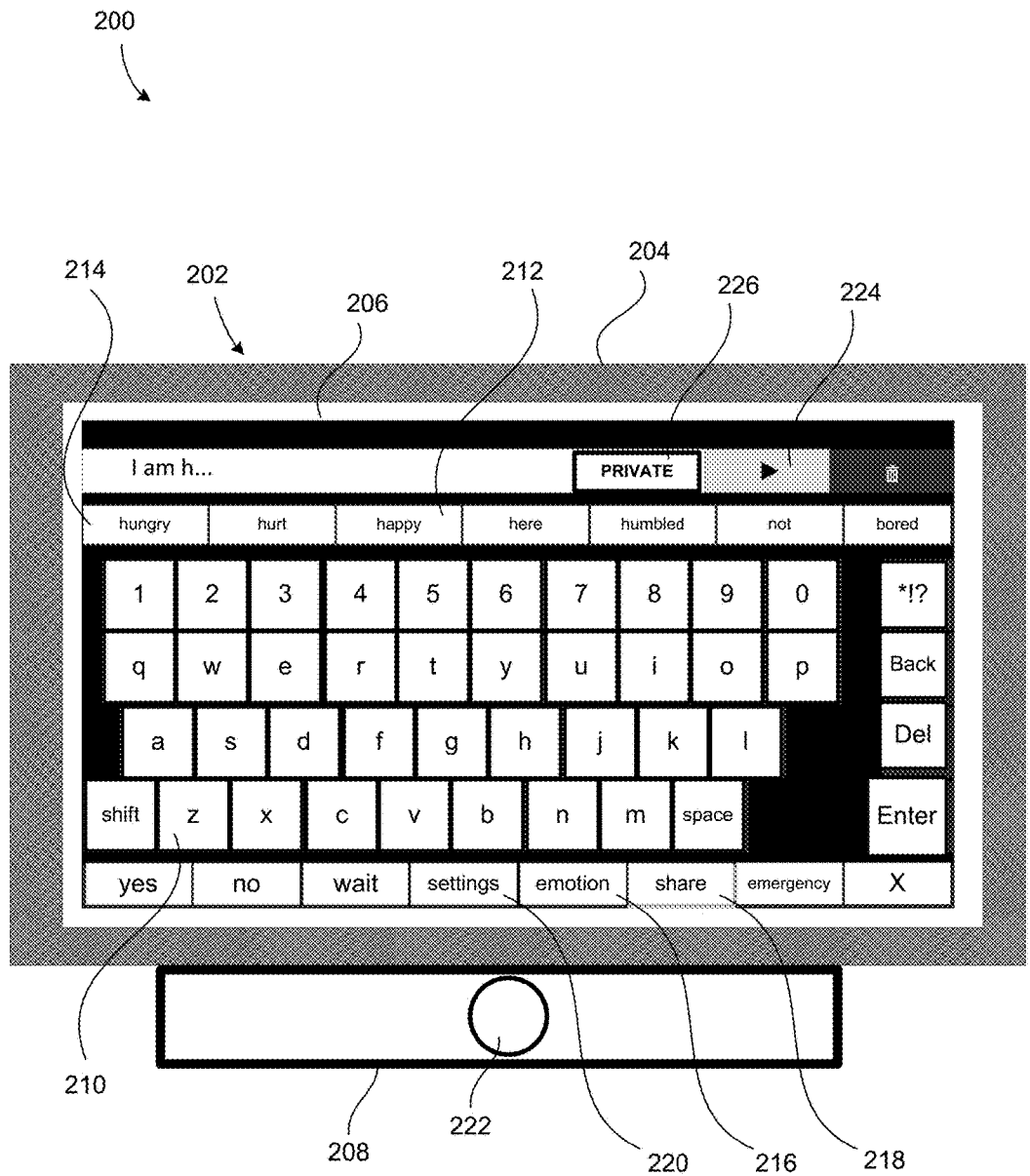
FIG. 2 depicts an example of a first display device and input device of a speech generating device.

FIGS. 2-5 depict different environments of a first display device of a speech generating device. In particular, FIG. 2 depicts an environment 200 having a first display device 204 and input device 208 of a speech generating device 202. In this non-limiting example, the first display device 204 includes a display screen 206 depicting a QWERTY keyboard and shortcut keys. The keyboard keys 210 and/or shortcut keys 212 may be programmable based on various factors such as the user's defined preferences, text recognition, or text prediction based on the context of the word or sentence being formed. For example, text prediction may be based on one or more factors: (1) the physical location of the SGD (as identified by a global positioning system (GPS) or any other location identifying technology) and any surrounding context that may be inferred from the identified location, (2) a SGD user's previous use or defined style of speaking in general, or (3) a SGD user's previous use or defined style of speaking with the specific conversation partner or group/circle of conversation partners. Additionally, or alternatively, one or more shortcut keys 212 may provide suggested text input from one or more conversation partners (discussed in greater detail below).

The SGD user may generate a message using the keyboard keys 210 and/or shortcut keys 212. The generated message may be publicly played through one or more speakers that are part of the SGD 202 or are connected to the SGD 202. The user may publicly play the message by selection the "play" key 224. In other examples, the user may select the "private" key 226 to discreetly send the message to one or more computing device of conversation partners over a communication network (e.g., via a server). Alternatively, the private message may be sent via a text, email, or notification to a computing device (e.g., second display device). In certain examples, the SGD may be programmed to send a private message to a certain conversation partner based on the time of day that the message is generated. In other examples, selection of the "private" key 226 may open a new window for the SGD user to select which conversation partner or social circle of conversation partners receives the message. In yet other examples, selection of the "private" key 226 may open a new window for the SGD user to select a social cue proxy to be displayed on the computing device or second display device identifying that the conversation partner should come to the SGD user to read the generated message on the display screen 206. In yet other examples, selection of the "private" key 226 may play the generated message at a reduced volume (that is at a volume level that is less than the standard/default volume level for the SGD). These examples are advantageous as it allows the SGD user to provide methods of public and discreet/private communication avenues.

In certain examples, one or more of the shortcut keys 212 may be programmable for accessing and selecting a social cue or emotional proxy for the user's generated communication. For example, a SGD user could select an "emotions" shortcut key 216 depicted in FIG. 2, wherein a new screen would be displayed with a number of depicted emotions for the user to choose from and attach with the generated message.

In additional examples, one or more of the shortcut keys 212 may be programmable to allow a SGD user to generate asynchronous or "offline" messages to share with one or more conversation partners when the conversation partner connects with the SGD user (e.g., when a computing device operated by the conversation partner connects with the SGD). For example, a SGD user could select the "share" shortcut key 218 on the display screen 206 to open a selection of options for sharing a message with a potential conversation partner at a later date. Further discussion for generating an asynchronous message is provided below with FIG. 3.

In other examples, one or more of the shortcut keys 212 may be programmable to allow a SGD user to access a selection of options for how messages are provided to conversation partners or which conversation partners receive a generated message. For example, a SGD user could select a "settings" shortcut key 220 on the display screen 206 to open a selection of options for directing communications to conversation partners, or for defining what conversation partners may see on their display device (e.g., the second display device). Further discussion for directed or discreet communication is provided below with FIG. 4.

In certain examples, one or more of the shortcut keys 212 may be programmable to allow a SGD user to access a selection of options for what conversation partners may review regarding past messages generated by a SGD user (e.g., whether a conversation partner may be able to review all previous messages generated by the SGD user, the last or most recent message generated by the SGD user, or no historical messages generated by the SGD user). For example, a SGD user could select the "settings" shortcut key 220 to open a selection of options for restricting or granting access to conversation partners for previous generated messages. Further discussion for access to previously generated messages is provided below with FIG. 5.

In certain examples, a conversation partner may discreetly assist the SGD user in composing the message in real-time. Through a connected computing device within a communication system or network, the conversation partner may be able to view the SGD user's generated message as it is being composed. In some examples, this may allow the conversation partner to view the message as it is being composed character-by-character, word-by-word, or sentence-by-sentence. The conversation partner may then be able to provide the user with suggested hints for the next word, phrase, or sentence. Additionally, or alternatively, the conversation partner may be able to provide suggested revisions or corrections to incorrectly typed words, phrases, or sentences.

This process may be completed discreetly using the connected computing device, wherein the conversation partner enters the word, phrase, or sentence on the computing device and transmits the suggestion to the connected speech generating device via a communication network (e.g., via a server). The processor and compatible software (e.g., computer program code) of the SGD analyzes the suggestion (or suggestions) provided by the conversation partner (or multiple conversation partners), and determines whether to replace one or more of the predictive text shortcut keys 212 with the conversation partner suggested text.

For example, as depicted in FIG. 2, the SGD user has begun composing a message, "I am h . . . ." A conversation partner may provide one or more suggestions for the next word. As depicted in this example, the top left shortcut key 214 includes the word "hungry," which was suggested by a conversation partner on a separate computing device, sent to the SGD, processed and inserted in the top left slot. Additional suggested text could be inserted into one or more of the remaining five shortcut key slots.

Suggested text (for predictions or corrections) may be regulated by the processor or software of the SGD. In certain examples, the SGD may be configured to regulate the number of suggestions possible. For example, a limited number of suggestions could be included (e.g., only one, two, or three suggestions from conversation partners maximum). In other words, the SGD may be configured (e.g., through its processor and software application) to analyze and determine which suggested text to include or discard if more suggestions are provided than available slots. For example, a suggestion from a conversation partner classified as a family member may be weighted more heavily than someone who is a work colleague. In other examples, the physical location of the SGD user may dictate which conversation partner's suggestion is provided more weight (e.g., a conversation in a hospital setting may weight a suggestion from a medical professional over family or friends).

The SGD may also be configured to grant or restrict certain conversation partners from providing suggestions. For example, conversation partners classified as family or friends may be granted permission to provide suggested text additions or corrections, while work colleagues may not. Again, the physical location of the SGD user may dictate whether a conversation partner is permitted to provide suggestions. For example, a work colleague or medical professional may be granted permission to make suggestions when the SGD user is at the office or at the hospital, respectively.

The SGD may also be configured to determine which shortcut key(s) to replace with the suggested word(s), phrase(s), or sentence(s) (e.g., the first shortcut key in the top left of the display screen 206, the last shortcut key in the top right of the display screen 206, or an internal shortcut key between the top left and the top right).

In certain examples, the suggested word, phrase, or sentence by the conversation partner may be highlighted or distinguished in some manner from the remaining predictive text shortcut keys 212 to identify that the conversation partner provided suggestion (e.g., font, color, or shortcut input key size). In certain examples, the suggested text is highlighted for a select number of conversation partners (e.g., family and/or friends only). Again, the physical location of the SGD user may dictate whether a suggestion is highlighted in one of the shortcut keys 212. For example, a suggestion from a work colleague or medical professional may be highlighted when the SGD user is at the office or at the hospital, respectively, as their suggestions may carry more weight in those environments.

In alternative examples, there is no distinguishing difference provided between a predictive text shortcut key and a suggested text shortcut key (e.g., the predictive text shortcut key and suggested text shortcut key have the same font, color, or shortcut input key size). This is advantageous as these suggestions appear merged into the standard predictive text selections on the SGD, thus allowing the user to preserve autonomy in choosing what to type, while at the same time providing contextually-appropriate suggested text options with the algorithmically-based predictive text options.

In other words, the ability for a conversation partner to provide suggested text on the display screen 206 of the SGD 202 is advantageous as it provides a subtle or discreet interaction between the SGD user and conversation partner. The SGD user is not interrupted by conversation partners guessing at what the user is typing. Additionally, the SGD user has control over the degree to which they utilize the suggested text from their conversation partners. Further, this interaction between SGD user and conversation partner has the benefit of further engaging conversation partners by providing them a method to directly interact with the generated communication as it unfolds in real-time rather than simply waiting for a block of communication to be completed before hearing it spoken by the system's generated speech. Also, in examples of providing suggested corrections of typographical errors in the SGD user's generated message, this may allow the SGD user to more efficiently make changes to the generated message before sending the message or playing it through the speakers of the device.

As depicted in FIG. 2, the input device 208 includes an eye gaze tracking device 222 positioned below the first display device 204. Other input devices are also possible (e.g., track pads, keyboards), and the position of the input device is configurable (e.g., positioned above the display device, positioned to the left or right side of the display device, or integrated with the display device itself). The input device 208 may be physically connected to the first display device 204, e.g., via a universal serial bus (USB)

connection, IEEE 1394 (FireWire) connection, Ethernet connection, DisplayPort, mini DisplayPort, or another physical connection technology, whether developed, in development, or future developed.

In some examples, the input device 208 is not physically connected to the first display device 204 of the speech generating device 202. Instead, the input device 208 may be remotely or wirelessly in communication with or connected to the speech generating device 202. The wireless connection may comply with a standard such as Bluetooth, IEEE 802.11 (wireless LAN), ultra-wide band (UWB) radio link, or infrared data association (IrDA) link.

To the extent the input device 208 includes an eye gaze tracking device 222, an eye controller with one or more light sources and sensing elements may be provided relative to the display device to identify and capture a user's selections. The first display device 204 may display visual objects that the user may select using the associated eye gaze tracking device 222. A processor and eye gaze tracking software associated with the speech generating device analyze data from the eye gaze tracking device 222 and select an object displayed on the display screen 206 of the display device 204. The tracking software may include an algorithm in conjunction with one or more selection methods to select an object on the display screen 206 of the speech generating device 202 by taking some action with one or both of the user's eyes.

Selection methods that may be activated using the eye gaze tracking device 222 to interact with the display screen 206 of the display device 204 may include eye gaze tracking software that analyzes eye blinking, dwelling, switching, or a combination thereof (e.g., blink/dwell, blink/switch, dwell/switch). Using a blink selection method, a selection will be performed when the user gazes at an object on the display screen 206 and then blinks for a specific length of time. The system may also interpret a "blink" as a set duration of time during which an associated camera cannot see the user's eye. The dwells selection method may be implemented when the user's gaze is stopped on an object on the display screen 206 for a minimum defined length of time. The blink/dwell selection combines the blink and dwell selection so that the object on the display screen 206 of the speech generating device 202 is selected either when the user's gaze is focused on the object for a specified length of time or if before that length of time elapses, the user blinks an eye. In the switch selection method, an object is selected when the user gazes on the object for a particular length of time and then closes an external switch. The blink/switch selection combines the blink and switch selection so that the object on the display screen 206 is selected when the user's gaze blinks on the object and the user then closes an external switch. Any number of commercial examples of eye gaze tracking devices are applicable. One example of an eye gaze tracking device is a Tobii EyeX sensor (available from Tobii AB, Danderyd, Sweden).

Figure 3:
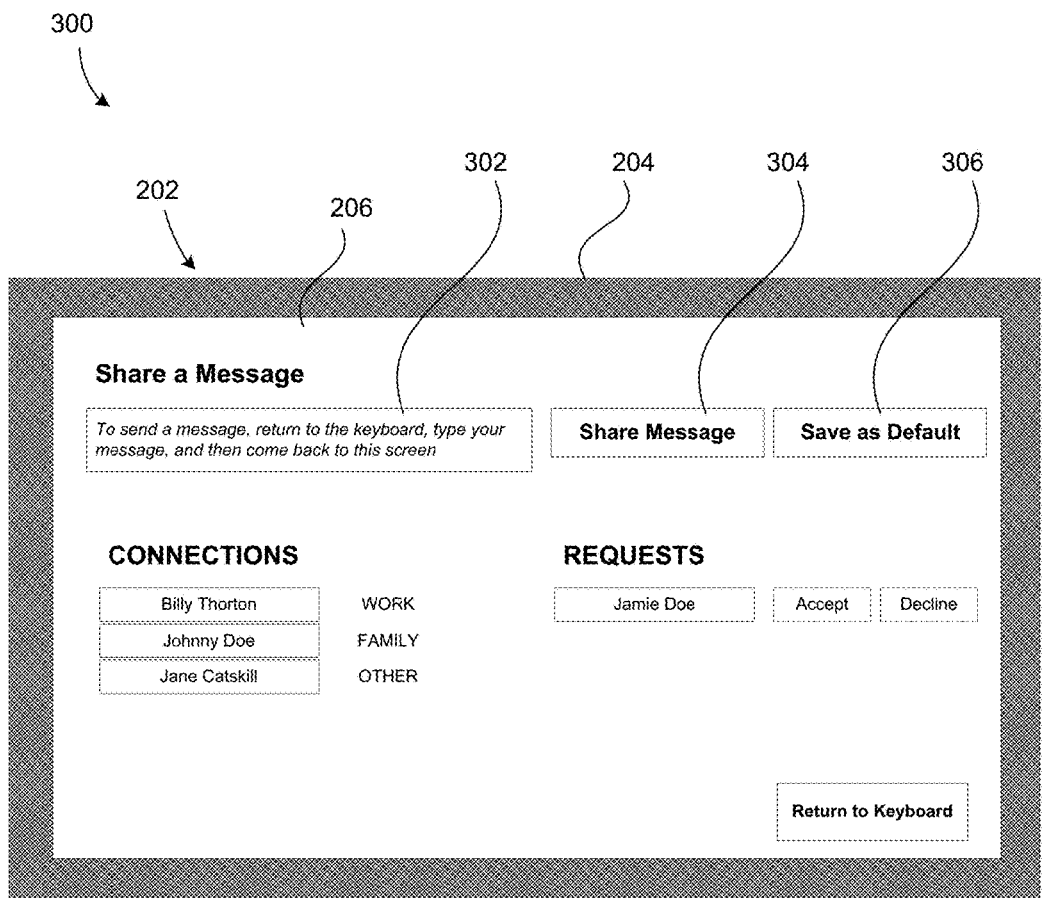
FIG. 3 depicts an example of communication requests and messages of a first display device of a speech generating device.

FIG. 3 depicts an environment 300 including the display screen 206 of the first display device 204 of a speech generating device 202. In this non-limiting example, the display screen 206 depicts options for the SGD user to generate and share messages 302 with a conversation partner or group of conversation partners. The display screen 206 of the first display device 204 may be accessed by a SGD user selecting a shortcut key on the display device (e.g., a "share" shortcut key 218 depicted in FIG. 2). In such examples, after a user has generated a message 302, the user may select an input key (e.g., a "share message" key 304 or a "save as default" key 306) on the display screen 206 to share the generated message with a selected conversation partner, a selected group of conversation partners, or all conversation partners. In certain examples, the message is shared on a second display device physically connected to the SGD such that a conversation partner within viewing range of the SGD (e.g., within the same room as the SGD user) may read the generated message displayed on the second display device.

In other examples, the user's generated message may be shared on one or more remotely or wirelessly connected display devices of selected conversation partners. In some examples, the generated message is shared with a conversation partner when the SGD user makes a request to connect with the conversation partner using the first display device of the SGD. Alternatively, a generated message may be shared with one or more conversation partners currently connected with the SGD user.

In certain examples, the generated message is shared with a conversation partner when the conversation partner connects with the SGD user or makes a request to connect with the SGD user using a second display device. In situations where an initial connection request has been made by a potential conversation partner, the SGD user may approve or reject the request. For example, FIG. 3 depicts a pending request from a potential conversation partner "Jamie Doe" to connect with the SGD user. Upon accepting the request, the SGD user may define a relationship category or social circle in which to place the conversation partner. This may include selecting a relationship category or social circle such as "Family," "Friends," "Work," "Medical," "Other," or any additional category the SGD user may create with their SGD. Following this relationship designation, the user's generated message may be sent to the second display device. In some examples, the SGD user may generate different messages for different conversation partners or different social circles. In such cases, a tailored message may be sent to the conversation partner upon connecting with the SGD user based on the defined relationship between the two individuals (e.g., one message may be sent to a work colleague conversation partner while a separate message may be sent to a medical personnel conversation partner).

The prepared or asynchronous message generated by the SGD user may be advantageous for several reasons. For one, the asynchronous message allows a SGD user to prepare communication content before a synchronous interaction occurs. This may allow a conversation partner to read the generated message while the SGD user is constructing additional speech for the current synchronous conversation, or the asynchronous message may offer content to fill a conversational gap that may occur due to the low throughput of communication.

In certain examples, the generated asynchronous message may include: (1) communication preferences of the SGD user, (2) a pre-composed block of text to initiate a conversation on a particular subject, (3) multimedia, or (4) activity data of the SGD user.

Regarding "communication preference" messages, this is a medium for the SGD user to express their preferred interactions and etiquette when communicating. For example, this could include messages such as, (1) "Please ask only yes or no questions;" (2) "Please do not look over my shoulder as I compose a message;" (3) "For private conversations, please read over my shoulder so I do not have to display my thoughts for all to hear;" (4) "Please do not finish my thoughts for me," or (5) "Please assist me in constructing my message through your mobile phone application."

These preferences are particularly useful as a form of conversation partner education, simplifying the process of instructing conversation partners in the specific communication strategies and preferences of any given SGD user. In certain examples, the communication preferences messages may be displayed on the second display device the first time a conversation partner connects with the SGD user. In other examples, the communication preferences are displayed or provided on the second display device each time a conversation partner connects with the SGD user, or each time a conversation partner connects with the SGD user after a period of time has elapsed (as a reminder of the SGD user's communication preferences). In certain examples, different communication preference messages may be provided to different conversation partners based on the defined relationship between the SGD user and conversation partner. For example, a SGD user may have certain communication preferences for work colleagues that differs from the communication preferences for medical personnel. Additionally, the SGD user may have certain communication preferences for requesting assistance in making corrections or suggestions to their message as the user composes the message in real-time (e.g., through a mobile phone software application that is in communication with the SGD).

A second type of asynchronous message is a "pre-composed block" message. These are general communications that the SGD user wishes to share with a conversation partner, but would like to prepare ahead of a synchronous conversation. These messages are advantageous as they allow the SGD user to compose longer or more complex thoughts than may be possible to construct during synchronous communication. These pre-composed block messages may be displayed on the second display device for viewing by a conversation partner. In some examples, in the case of a remotely or wirelessly connected computing device, the pre-composed block message may be displayed on the display device of the separate computing device when the conversation partner connects with the SGD user. This connection may occur when the conversation partner opens an application on the computing device in preparation for having a conversation with the SGD user. In certain examples, different pre-composed block messages may be provided to different conversation partners based on the defined relationship between the SGD user and conversation partner.

A third type of asynchronous message is a "multimedia" message. Multimedia messages allow a SGD user to take pictures using their SGD device (e.g., through eye gaze selection of a camera-icon keyboard key on the display screen). Multimedia messages also allow for a SGD user to select any form of multimedia content (e.g., audio or video content). The multimedia content (e.g., picture) may be displayed on a second display device of the SGD or sent to a selected conversation partner operating a separate computing device having a display device. This is advantageous as the multimedia message provides the SGD user with a rich channel for sharing their experiences with others. This may increase conversation throughput by reducing the need to type descriptions of visual scenes. In other words, "a picture is worth a thousand words." In certain examples, different multimedia may be provided to different conversation partners based on the defined relationship between the SGD user and conversation partner.

A fourth type of asynchronous message is an "activity data" message. Activity data may include, for example, a user's recent web browsing history, television- or movie-watching history, book reading or listening history, music listening history, article reading history, or application usage history on their SGD or connected device. The activity data may be collected and stored for a defined period of time (e.g., the last hour, 2 hours, 4 hours, 8 hours, 12 hours, 24 hours, 1 week). In some examples, the defined period of time may be the time interval since the SGD user and conversation partner last connected. The activity data from the defined period of time may be displayed on a second display device of the SGD or sent to a selected conversation partner operating a separate computing device having a display device. This is advantageous as the activity data message provides the SGD user with a channel for sharing their recent experiences with others. For example, the conversation partner may see that the SGD user watched a movie on their device after they last connected. The conversation partner may be able to skip the question "What have you been up to?" and dive right into questions about the movie. This may increase conversation throughput by reducing the need to have an introductory-type conversation. In certain examples, different activity data messages may be provided to different conversation partners based on the defined relationship between the SGD user and conversation partner.

Figure 4:
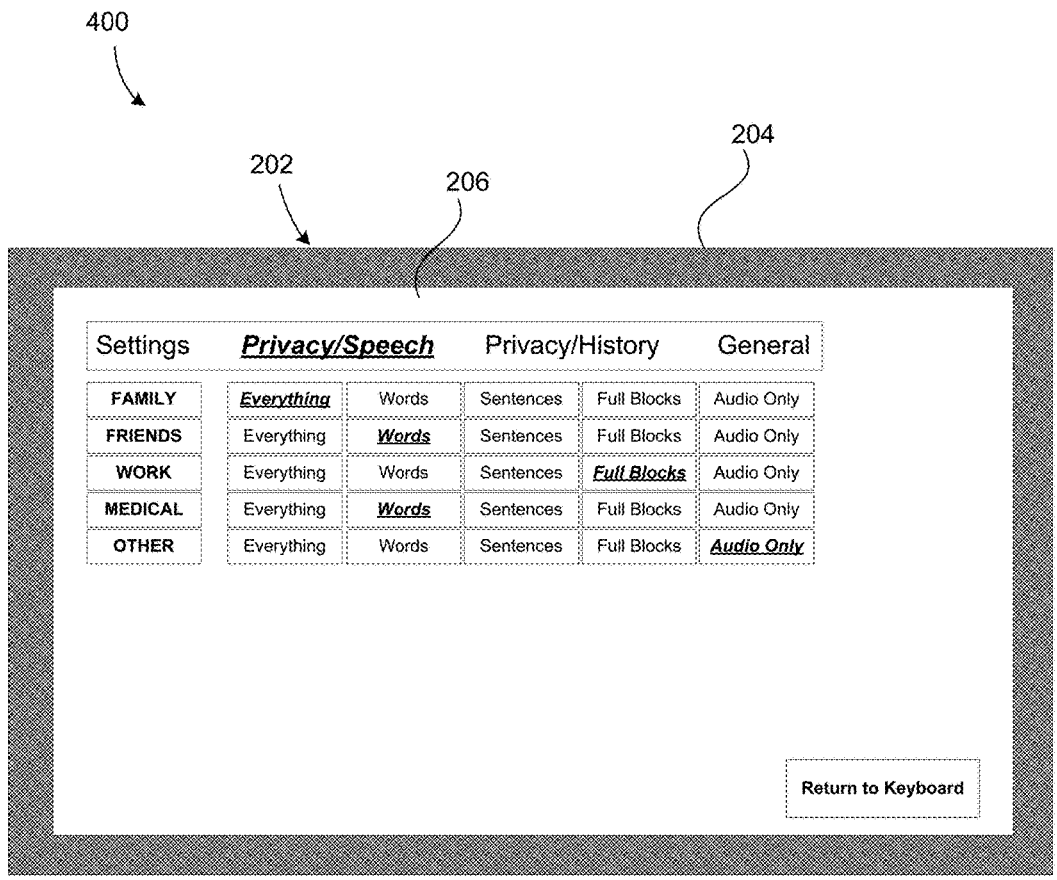
FIG. 4 depicts an example of privacy and speech settings of a first display device of a speech generating device.

FIG. 4 depicts an environment 400 including a display screen 206 of a first display device 204 of a speech generating device 202. In this non-limiting example, the display screen 206 depicts "levels of sharing" for the SGD user to define what a conversation partner or group of conversation partners may be able to view as the SGD user generates a message. The display screen 206 of the first display device 204 may be accessed by a SGD user selecting a shortcut key on the display device (e.g., a "settings" shortcut key 220 depicted in FIG. 2).

This "levels of sharing" feature is advantageous as it allows a SGD user to decide what granularity of communication data the conversation partner is able to view on a connected computing device having a display screen. This provides a SGD user with the ability to retain control or autonomy of how the user communicates with others.

Additionally, this feature provides a balance between two competing issues. First, generation of a message using the SGD may be relatively slow and tedious. Therefore, requiring the SGD user to explicitly set privacy permissions for every connected conversation partner may make the system too tedious to use. Second, a SGD user may want to share different amounts of information with different types of conversation partners (e.g., share more information with family and less with general acquaintances).

Therefore, SGD users may classify conversation partners into social circles and set privacy permissions for entire circles rather than individual partners. As previously noted, a conversation partner may be initially classified into a specific circle following the initial request and acceptance to communicate through the communication system. Examples of social circles include "Family," "Friends," "Work," "Medical," and "Other." Additional circles may be programmable by the SGD user using the installed communication software on the SGD.

This classification of conversation partners into circles may function both as a user management feature and a privacy feature. In certain examples, a potential conversation partner has to request to connect with the SGD user through an application on their computing device and then the SGD user has to approve the request and place the conversation partner into a social circle. Only at this stage will the conversation partner be able to see any conversations generated by the SGD user on the connected speech generating device. In other examples, the SGD user may make the initial request to connect with a conversation partner and establish the social circle for the potential conversation partner.

As depicted in FIG. 4, a SGD user may use an interface to set the permissions for an entire circle of conversation partners. This allows the SGD user to limit the amount of information presented in the real-time view of synchronous messages on the computing device of the circles of conversation partners. For example, the SGD user may allow a specific group or circle of conversation partners to view updates for a generated communication character-by-character, word-by-word, sentence-by-sentence, block-by-block (e.g., fully composed thoughts), or to only show status information (e.g., social cue information) and not show text at all. In some examples, default settings may be provided for each circle in order to reduce the amount of effort required from a SGD user. For example, as depicted in FIG. 4, conversation partners classified as "Family" may view a SGD user's message as it is generated character-by-character, while "Friends" and "Medical" may receive updates word-by-word, "Work" may receive updates block-by-block, and "Other" may receive audio only.

Figure 5:
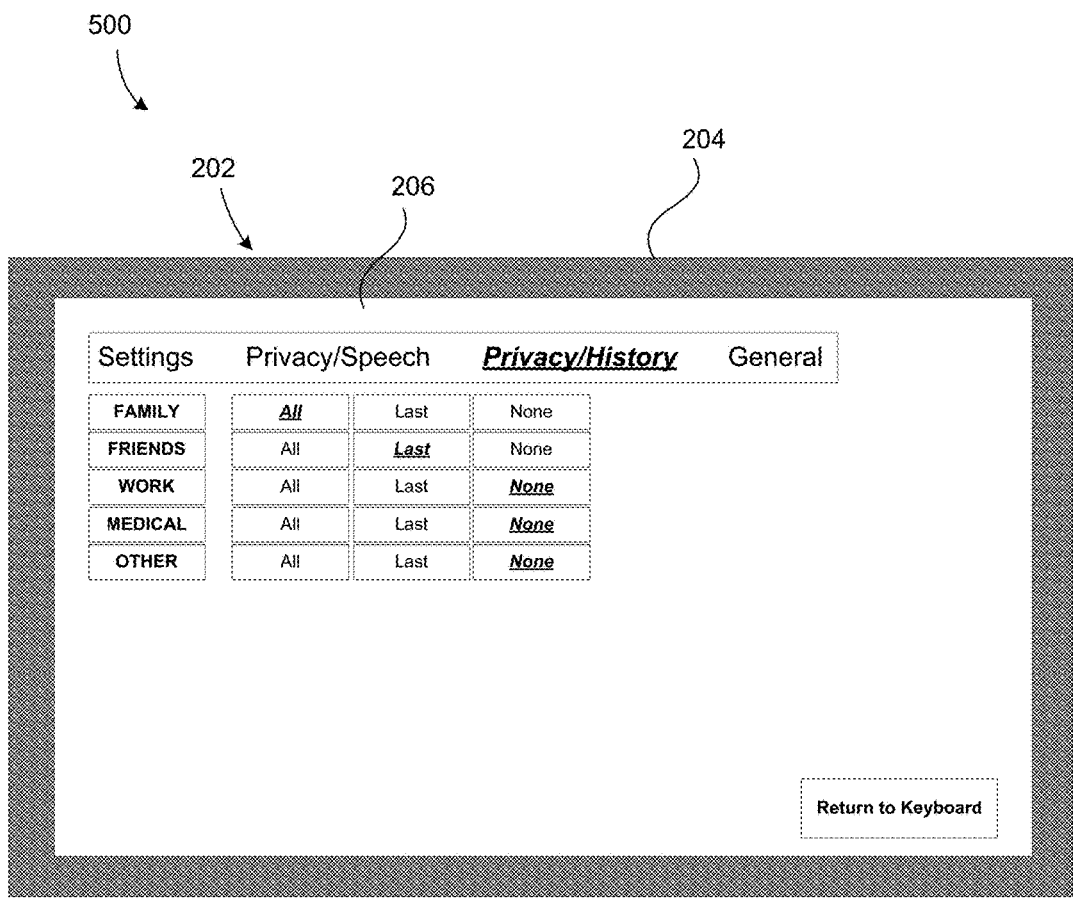
FIG. 5 depicts an example of privacy and history settings of a first display device of a speech generating device.

FIG. 5 depicts an environment 500 including a display screen 206 of a first display device 204 of a speech generating device 202. In this non-limiting example, the display screen 206 depicts "levels of sharing" for historical or previously generated messages. In this example, the SGD user may define what previous message or messages a conversation partner or group of conversation partners may be able to view (e.g., "All" of the SGD user's generated messages, only the "Last" or most recent message generated, or "None" of the user's generated messages). The display screen 206 of the first display device 204 may be accessed by a SGD user selecting a shortcut key on the display device (e.g., a "settings" shortcut key 220 depicted in FIG. 2).

This "levels of sharing" feature for a SGD user's history is advantageous as it allows a SGD user to decide what level of context to provide to a conversation partner or a group of conversation partners. This provides a SGD user with the ability to retain control or autonomy of how the user communicates with others. This feature also provides the ability to update a more intimate conversation partner (e.g., family or friend) on what the SGD user has been talking about recently, without having to regenerate the message.

For example, as depicted in FIG. 5, conversation partners designated as "Family" may be able to view a SGD user's entire history of generated messages, allowing family members to catch up on any conversations that the user recently generated. Additionally, conversations partners designated as "Friends" may be able to view a SGD user's last or most recently generated message, allowing friends to view what the SGD user was recently talking about, possibly allowing the friend to develop a conversation with the SGD user about the same topic with some background understanding in place.

Figure 6:
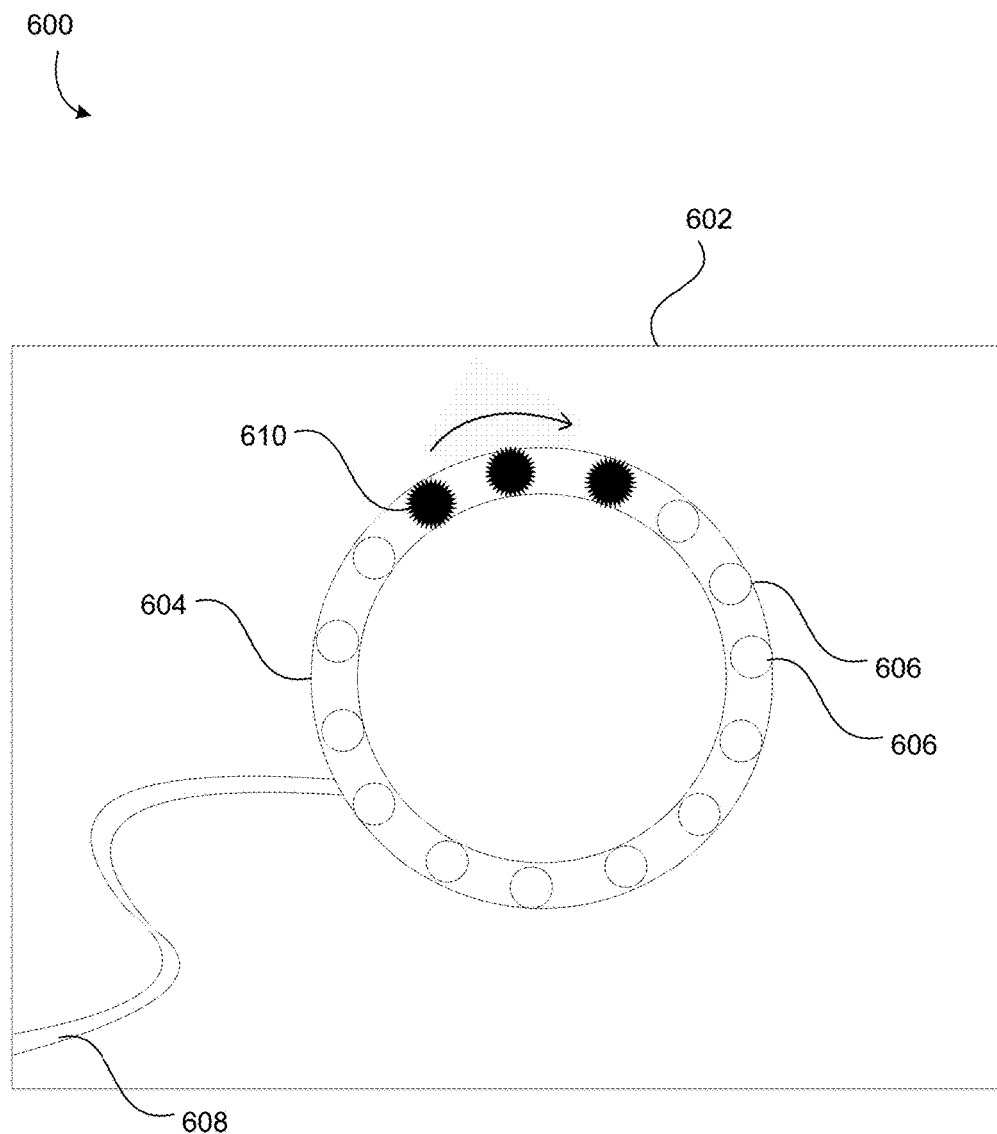
FIG. 6 depicts an example of a second display device of a speech generating device or communication system.
Figure 7:
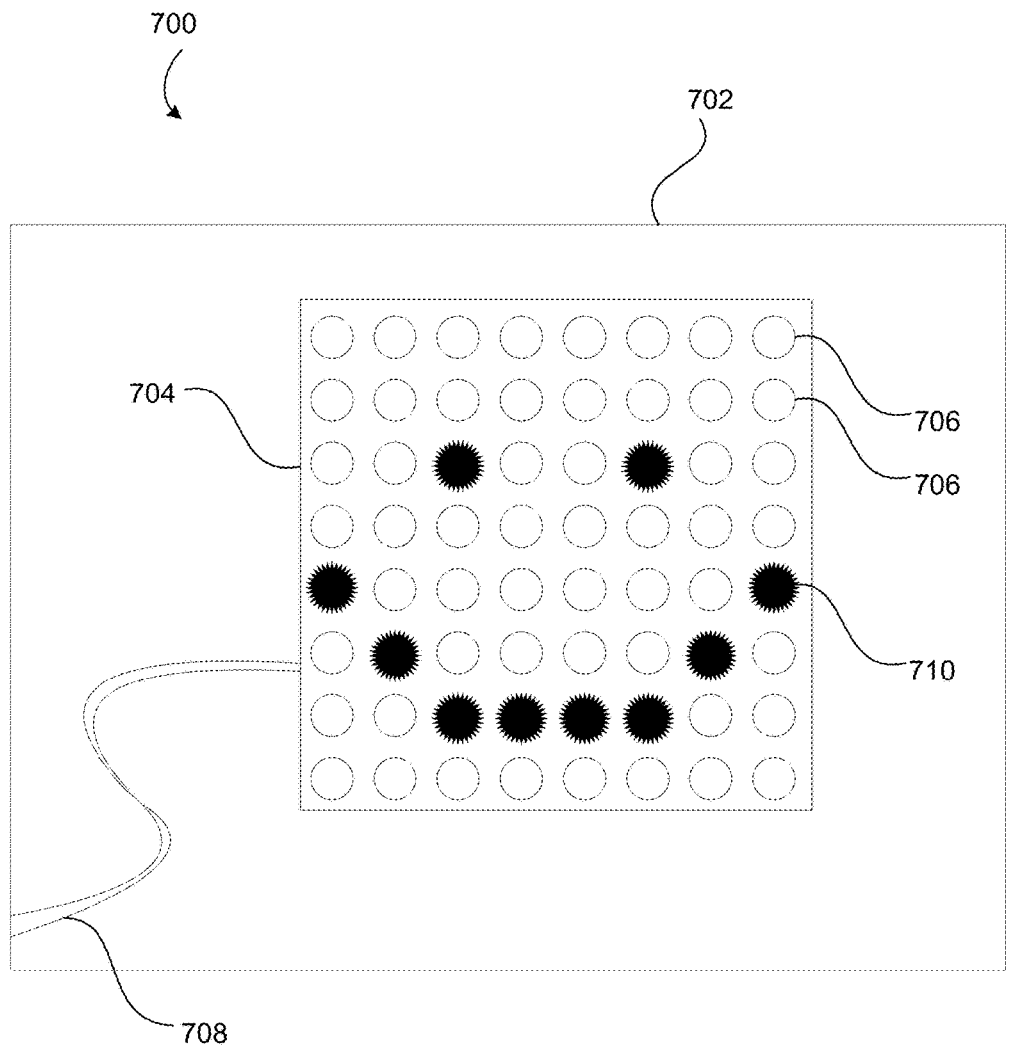
FIG. 7 depicts an additional example of a second display device of a speech generating device or communication system.
Figure 7:
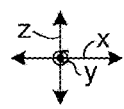
Figure 8:
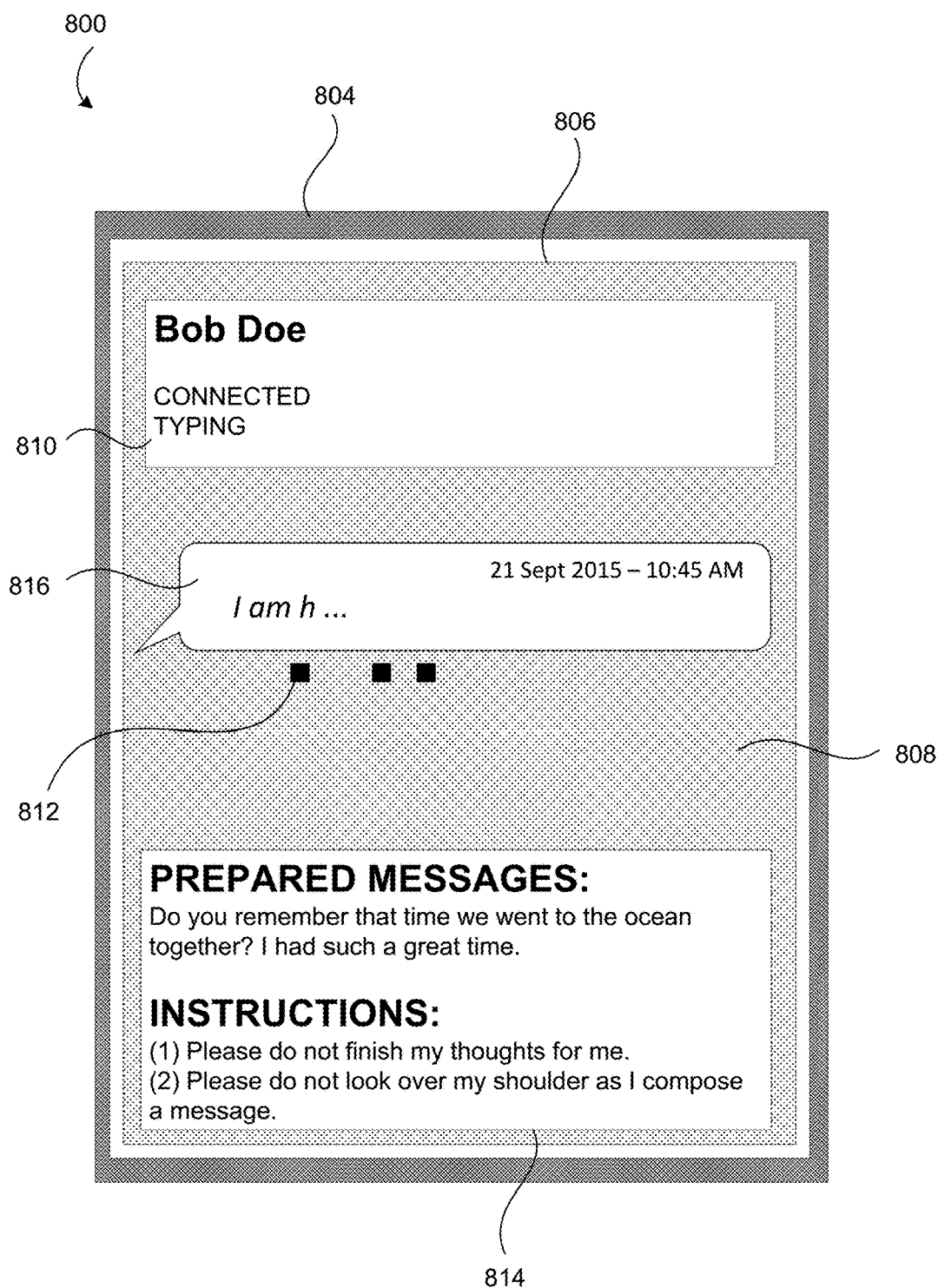
FIG. 8 depicts an additional example of a second display device of a speech generating device or communication system.

FIGS. 6-8 depict various non-limiting examples of a second display device of a communication system. In certain examples, the second display device is physically connected to and part of the SGD. In other examples, the second display device is separate from and remotely or wirelessly in communication with the SGD.

For example, FIG. 6 depicts an environment 600 of a second display device 604 positioned on a surface of a SGD 602. The second display device 604 is positioned such that the second display device 604 faces in a separate direction from the direction of the first display device of the SGD 602. In this example, the second display device 604 is positioned along the x-z plane and the display is being directed along the y-axis extending from the page. The first display device may be on the opposite surface of the SGD 602, wherein the first display device is also positioned along the x-z plane and the display from the first display device is also directed along the y-axis, but extending into the page.

The second display device 604 includes an array of lighting elements 606. The elements 606 may be light emitting diodes (LEDs) (e.g., organic LEDs), or another emission technology, whether developed, in development, or future developed, may be used. Each element of the lighting elements 306 may include an array of pixels (including, e.g., a plurality of subpixels) to display a variety of colors.

In this example, the array of lights 606 forms a circular shape on the surface of the SGD 602. The array of lights 606 may be a strip of LED lights. Other formations are also possible (see FIG. 4, for example). In the depicted example in FIG. 6, the plurality of lighting elements are physically connected to the SGD via a connector 608 (e.g., cable). The cable 608 may be externally connected on or above the surface of the SGD 602 or internally connected beneath the surface of the SGD 602. The cable 608 may be connected to the SGD 602 via a universal serial bus (USB) connection, IEEE 1394 (FireWire) connection, Ethernet connection, DisplayPort, mini DisplayPort, or another physical connection technology, whether developed, in development, or future developed.

In alternative examples, the second display device 604 is not physically connected to the SGD 602. Instead, the second display device 604 may be remotely or wirelessly in communication with or connected to the speech generating device 602. The wireless connection may comply with a standard such as Bluetooth, IEEE 802.11 (wireless LAN), ultra-wide band (UWB) radio link, or infrared data association (IrDA) link.

The second display device 604 may operate in conjunction with the first display device of the SGD. As the user is preparing a communication, or after the user has completed and "spoken" or played the communication through the speakers of the SGD 602, the second display device 604 may identify and display a proxy for a social cue or emotion of the SGD user regarding the communication.

The social cue or emotional proxy of the SGD user may be provided by different lighting configurations or colors, for example. As depicted in FIG. 6, three lighting elements 610 are illuminated and are rotated around the circle, which may provide a social cue proxy to a conversation partner that the user is typing a message. Further examples of social cue and emotional proxies are discussed in greater detail below.

As noted, the positioning of the second display device 604 may allow the conversation partner to view the user of the SGD 602 face-to-face like a conventional conversation, instead of looking over the shoulder of the user as they operate the SGD 602. Additionally, through the social cue or emotional proxy identified on the second display device 604, the conversation partner may be aware of the user's communication status or emotion.

FIG. 7 depicts an additional environment 700 of a second display device 704 positioned on a surface of a SGD 702. The environment in FIG. 7 is similar to FIG. 6, except for the design of the lighting elements 706 being in a rectangular shape. Through this design, social cue proxies and emotional proxies may be identified in separate or similar arrangements from the proxies used in the circular design of FIG. 6. As depicted in FIG. 7, several lighting elements 710 are illuminated to portray a smile, which may provide an emotional proxy to a conversation partner that the user is happy or the message is meant to be humorous. Further examples of social cue and emotional proxies are discussed in greater detail below.

In this depicted example in FIG. 7, the plurality of lighting elements 706 are physically connected to the SGD via a connector 708 (e.g., cable). The cable 708 may be externally connected on or above the surface of the SGD 702 or internally connected beneath the surface of the SGD 702. The cable 708 may be connected to the SGD 702 via a universal serial bus (USB) connection, IEEE 1394 (FireWire) connection, Ethernet connection, DisplayPort, mini DisplayPort, or another physical connection technology, whether developed, in development, or future developed.

Like the example in FIG. 6, the second display device 704 in FIG. 7 is positioned such that the second display device 704 faces in a separate direction from the direction of the first display device of the SGD 702. In this example, the second display device 704 is positioned along the x-z plane and the display is being directed along the y-axis extending from the page. The first display device may be on the opposite surface of the SGD 702, wherein the first display device is also positioned along the x-z plane and the display from the first display device is also directed along the y-axis, but extending into the page.

FIG. 8 depicts an environment 800 of a second display device 804 of a communication system or SGD. In this example, the second display device 804 may be part of the SGD and positioned on a surface of a SGD. Alternatively, the second display device 804 depicted in FIG. 8 may be part of a device physically separate from the SGD, wherein the separate device is part of the communication system and is remotely or wirelessly connected with the SGD. The wireless connection may comply with a standard such as Bluetooth, IEEE 802.11 (wireless LAN), ultra-wide band (UWB) radio link, or infrared data association (IrDA) link.

For example, the second display device 804 may be part of a computing device separate from the SGD. The computing device may be a personal computer (PC), server computer, tablet and other handheld computing device, laptop or mobile computer, communications device such as a mobile phone (e.g., smartphone), multiprocessor system, microprocessor-based systems, set top box, programmable consumer electronic, network PC, minicomputer, mainframe computer, or audio or video media player. In certain examples, the computing device may be a wearable electronic device, wherein the device may be worn on or attached to a person's body or clothing. The wearable device may be attached to a person's shirt or jacket; worn on a person's wrist, ankle, waist, or head; or worn over their eyes or ears. Such wearable devices may include a watch, heart-rate monitor, activity tracker, or head-mounted display.

As depicted in FIG. 8, the second display device 804 includes a display screen 806. The display screen 806 may include a light emitting device such as an electronic-paper display, a liquid crystal display (LCD), a light emitting diode (LED) (e.g., an organic light emitting diode (OLED)), or a standard graphics display. The LCD or LED may be disposed in, or configured as, a film. The configuration, construction, materials, and other aspects of the light emitting devices may vary. Non-LED technologies, such as finely tuned quantum dot-based emission structures, may also be used. Other thin form factor emission technologies, whether developed, in development, or future developed, may be used.

The display screen 806 of the second display device 804 may include an array of pixels (including a plurality of subpixels) to display the various colors of an image. In certain examples, the second display device 804 may operate in conjunction with the first display device of the SGD to display a social cue or emotional proxy of the user. For example, as the user is preparing a communication, or after the user has completed and "spoken" or played the communication through the speakers of the SGD, the second display device 804 may identify and display a social cue or emotion of the SGD user regarding the communication on the display screen 806.

The social cue or emotional proxy may be provided by different lighting configurations, colors, emoji, images, graphics, or avatars on the display screen. For example, the background 808 of the display screen 806 may be changed to a specific color (e.g., red) to function as an emotional proxy (e.g., anger) of the SGD user's message. Additionally or alternatively, the display screen 806 may provide context such as text 810 of the social cue, e.g., "Bob is typing" or "Bob is talking." In some examples, the social cue may be provided in a unique pattern of lights or colors, such as those described above with FIGS. 7 and 8. For example, the indication that the SGD user is typing may be depicted by a series of three dots 812 moving horizontally across the display screen 806. Additional examples of social cue and emotional proxies are discussed below.

The second display device 804 may also display helpful information 814 to the conversation partner to assist in communicating with the SGD user. For example, a SGD user may generate one or more asynchronous or "offline" messages 814 to share on the display screen 806 of the second display device 804. In certain examples, the asynchronous message is shared on the physically connected second display device 804 of the SGD. In other examples, the asynchronous message is shared on the remotely or wirelessly connected second display device 804 when the device connects with the SGD (e.g., through a compatible application installed on the computing device, such as when the conversation partner opens the application to connect with the SGD).

In certain examples, as previously discussed, the generated asynchronous message 814 to be displayed on the display screen 806 may include: (1) communication preferences of the SGD user, (2) a pre-composed block of text to initiate a conversation on a particular subject, (3) multimedia, or (4) activity data. Regarding "communication preference" messages, this is a medium for the SGD user to express their preferred interactions and etiquette when communicating. These are particularly useful as a form of conversation partner education, simplifying the process of instructing conversation partners in the specific communication strategies and preferences of any given SGD user. Regarding "pre-composed block" messages, these messages are advantageous as they allow the SGD user to compose longer or more complex thoughts than may be possible to construct during synchronous communication. Additionally, "multimedia" messages may allow a SGD user to take pictures or video using their SGD device, providing the SGD user with a rich channel for sharing their experiences with others, and therein increasing conversation throughput by reducing the need to type descriptions of visual scenes. Further, activity data messages may allow a SGD user to share their recent experiences with others.

In some examples, the display screen 806 may provide the communicated message in real-time as the message is being prepared by the user or after the message has been completed and spoken through the speakers of the SGD or separate computing device. Based on the defined relationship or social circle between the SGD user and communication partner, the real-time message may be provided on the display screen character-by-character, word-by-word, sentence-by-sentence, block-by-block (e.g., fully composed thoughts), or to only show status information (e.g., social cue information) and not show text at all. This is advantageous as it allows certain conversation partners to more fully engage with the SGD user in a synchronous communication. This provides conversation partners with an accurate mental model of the ongoing communication and potentially allows the conversation partner to better understand what the SGD user is attempting to say. Additionally, this feature provides that communication partners do not need to read over the shoulder of the SGD user when unsure of what the SGD user is attempting to write.

As previously noted, in certain examples, the second display device 804 may be configured to assist the SGD user in composing the synchronous message. When the second display device 804 or computing device is connected to the SGD, a conversation partner may be able to view the SGD user's generated message as it is being composed. In some examples, this may allow the conversation partner to view the message as it is being composed character-by-character, word-by-word, or sentence-by-sentence. The conversation partner may then be able to provide the user with suggested hints for the next word, phrase, or sentence. In other words, the conversation partner may enter words, phrases, or sentences on the second display device 804 and send them to the SGD for consideration.

For example, as depicted in FIG. 8, the display screen 806 indicates that the SGD user has begun composing a message, "I am h . . ." A conversation partner may enter one or more suggestions for the next word, (e.g., "hungry," "here," "hurt") using the second display device 804 and send those suggestions to the SGD. This process is advantageous as the conversation partner is providing "discreet" suggestions to the SGD user through the connected devices. This respects the autonomy of the SGD user while leveraging the contextual knowledge and shared history of the conversation partner to potentially improve communication.

In other words, the ability for a conversation partner to provide suggested words, phrases, or sentences on the SGD is advantageous as it provides a subtle or discreet interaction between the SGD user and conversation partner. The SGD user is not interrupted by conversation partners guessing at what the user is typing. Additionally, the SGD user has control over the degree to which they utilize the suggested text from their conversation partners. Further, this interaction between SGD user and conversation partner has the benefit of further engaging conversation partners by providing them a method to directly interact with the generated communication as it unfolds in real-time rather than simply waiting for a block of communication to be completed before hearing it spoken by the system's generated speech.

In examples where the second display device 804 is part of a computing device separate from the SGD, the second display device 804 or computing device may include its own processor and/or software (e.g., computer program code) configured to communicate with the SGD. In certain examples, software may be installed on the computing device (e.g., mobile phone) that is compatible with communicating with the software installed on the SGD. In some examples, the software application may be developed using HTML5 and JavaScript in the Apache Cordova framework, allowing it to run on a Windows Phone, Android phone, and iOS phone. Communication between the SGD software and the software application on the separate communication device may be facilitated through a real-time NoSQL database system.

Additionally, in examples where the second display device 804 is part of a computing device separate from the SGD, the second display device 804 or computing device may include one or more speakers configured to play a message generated by the SGD user on the SGD. In other examples, the second display device 804 or computing device may be connected to or in communication with one or more speakers of a separate audio-playing device (e.g., headphones, wired or wireless speakers such as a Bluetooth audio speaker) to play the device. This is advantageous as audio playback on the computing device (e.g., mobile phone) or a connected audio-playing device allows the SGD user to choose how or where their generated message is played (e.g., the conversation partner may not necessarily be in the same room). In some examples, the SGD user may select to play their message publicly on their own device, wherein the message is audible to other people within the same room or a certain distance speaker(s) of the SGD. In other examples, the SGD user may select to play their generated message to a connected communication partner or a group of communication partners (e.g., within the same social circle). This is advantageous as it allows the SGD user to decide whether or not they wish to have a public conversation, a private/side conversation within the same room, or a remote conversation with a conversation partner in a different location than the user. In other words, in conjunction with a connected communication partner's ability to receive real-time views of the user's generated messages, the mobile audio provides telephony-like long distance communication for a SGD user.

Social Cue Proxies

In certain examples, the user of the speech generating device may select a social cue proxy to display on the second display screen. In other examples, the displayed social cue proxy may be determined based on a SGD processor/software analysis. As discussed in detail below, the social cue proxy may be (1) indicating that the user is typing or composing a message, (2) indicating that the user is speaking or about to speak, (3) indicating that the user is requesting to speak, (4) requesting assistance, (5) identifying an emergency, (6) indicating that the user is calibrating the input device of the SGD (e.g., calibrating the eye gaze tracking device), (7) indicating that the SGD is idle, or (8) indicating that the SGD user's eyes are closed (e.g., sleeping).

To begin, one social cue proxy is an indicator that the user of the SGD is composing a message. This social cue proxy is advantageous in that it allows the conversation partner to know that the SGD user is actively engaged in the conversation, or is attempting to initiate a conversation with the conversation partner. The conversation partner may have asked the SGD user a question, and may not be able to tell from the user's facial expressions or body movements (or lack thereof) whether the user is attempting to respond to the question. The indication that the user is typing or replying to the question potentially avoids the conversation partner from re-asking the question, asking a new question, moving over to look over the shoulder of the user, or leaving the room prematurely. Furthermore, to the extent the second display device provides no proxy that the user is actively typing, the conversation partner may understand that he or she needs to repeat the question or examine if the user's speech generating device is functioning properly.

In some examples, the user may select the social cue proxy to be displayed by the second display device. Alternatively, the processor of the SGD may analyze that the user is composing a message and display the social cue proxy indicating the user is composing a message. For example, once the user begins to compose the message using the input device, the indicator or social cue proxy may be displayed on the second display device. The indicator may be a unique color, flashing lights or series of light movements (e.g., three lights rotating around the circular array of lighting elements in FIG. 3), or a message on a screen of the second display device indicating, (e.g., "Bob is typing"). The indicator may remain displayed on the second display device as long as the user is typing. The processor or software of the SGD may have a predefined time-out period, wherein the indicator remains displayed so long as the user is actively searching for the next word, character, or image within the predefined time period (e.g., a character, word, or image in 1 minute, 30 seconds, 15 seconds, 10 seconds, or 5 seconds).

A second social cue proxy is an indicator that the user of the SGD is speaking or about to speak (e.g., the user is about to play a message through the speakers of the SGD). This social cue proxy is advantageous in that it alerts the conversation partner to pay attention to the user and listen to the message. In this example, the user may select the social cue proxy to be indicated on the second display device, or the processor may provide the indication that the user is speaking or about to speak (e.g., after the user submits the message to be played through the speakers of the SGD). In certain examples, once the user submits the message, the indicator may be displayed on the second display device. The indicator may be a unique color, flashing lights or series of light movements, or a message on a screen of the second display device indicating, e.g., "Bob is about to speak" or "Bob is speaking." In some examples, the second display device includes a plurality of illuminated lights (e.g., LEDs) in a single color, wherein the intensity of the lights goes up and down as the message is played (e.g., wherein the intensity of the lights flows with the words being spoken through the speakers). In other examples, in order to get the attention of the conversation partner, the second display may provide an indication (e.g., one or more flashes of light) that the user is about to speak. The indicator or proxy may remain displayed on the second display device as long as the user is speaking.

A third social cue proxy is a request to speak. This social cue proxy is advantageous in that it allows the conversation partner (or partners) to know that the SGD user would like to add something to the conversation. Due to particularly slower speeds of communication using a SGD, the user may feel left out of a conversation with more than one conversation partner. The user may have something to add to the conversation, but has difficulty "jumping in." Through a social cue proxy of requesting to speak, the user is "raising their hand" to be called on, allowing their opinion to be heard. Like the previous examples, the user may directly make a request to speak by selecting certain text or an image on the first display screen of the SGD, therein creating an indication on the second display device. Alternatively, the software or processor of the SGD may determine that the user would like to speak with the conversation partner. In some examples, the user may compose a message before, during, or after the social cue proxy for a request to speak has been initiated. Therefore, in some examples, after being acknowledged by the conversation partner(s), the user may play their composed message through the speakers of the SGD without noticeable delay in the speed of the conversation. Like the other previously described social cue examples, the indicator for the request to speak may be a unique color, flashing lights or series of light movements, or a message on a screen of the second display device indicating, e.g., "Bob would like to speak." The indicator may remain displayed on the second display device until cleared by the user or the conversation partner/attendant, or until a predefined time has expired.

A fourth social cue proxy is a request for help or a request to read a discreet message from a conversation partner, e.g., an attendant such as a nurse or hospital administrator. This social cue proxy is advantageous in that it allows the conversation partner to know that the SGD user needs help from or would privately like to speak with the conversation partner or attendant without having to play a message through the speakers of the SGD where the message may be heard by others in the area. In this example, the user may directly request help or request for the conversation partner to read a discreet message through an indication on the second display device or move into a separate room for a private conversation. Alternatively, the software or processor of the SGD may determine that the user requires assistance from the conversation partner. For example, the SGD user may compose a message requesting assistance or a discreet conversation. The software and processor of the SGD may analyze the message and understand that help or a discreet conversation is being requested. Alternatively, help may be requested due to a perceived error in the SGD. For example, the speech generating device may not be operating properly (e.g., the speech generating software program may be frozen or a pop-up window on a display screen of the first display device may be preventing the user from composing a message.) The social cue proxy or indicator may be displayed on the second display device acknowledging that a request for help or a request for a discreet communication has been made. The indicator may be a unique color (e.g., blue), flashing lights or series of light movements, or a message on a screen of the second display device indicating, e.g., "Bob would like your assistance" or "Bob would like to speak with you privately." The indicator may remain displayed on the second display device until cleared by the user or the conversation partner/attendant, or until a predefined time has expired.

A fifth social cue proxy is an indication that there is an emergency requiring immediate attention. This social cue proxy is advantageous in that it allows the conversation partner to know that the SGD user needs immediate help. Again, the user may select the emergency indication to be displayed on the second display device, or the processor of the SGD may determine that an emergency situation exists. For example, the SGD may be part of a communication system that includes other devices, such as a heart rate monitor or other health monitoring equipment. The heart rate monitor or other health monitoring equipment may detect an anomaly in the user's health status, and the SGD may receive the indication of the anomaly. The SGD may then alert a conversation partner to the emergency issue via the second display device. The indicator on the second display device may be a unique color (e.g., red), flashing lights or series of light movements, or a message on a screen of the second display device indicating, e.g., "EMERGENCY." The indicator may remain displayed on the second display device until cleared by the user or an attendant, until a predefined time has expired, or until the health monitoring equipment indicates a non-emergency reading.

A sixth social cue proxy is an indication that the user is attempting to calibrate the input device of the SGD. For example, the user may occasionally need to calibrate an eye gaze tracking device or a touchscreen input, for example, to create or maintain accurate input. This social cue proxy is advantageous in that it allows the conversation partner to know that the SGD is busy, and that it may be some time before the user is able to generate a message or respond to a question from the conversation partner. In this example, the processor or software of the SGD may determine that the device is undergoing calibration testing. The indicator on the second display device may be a unique color indicating the input device of the SGD is being calibrated, flashing lights or series of light movements, or a message on a screen of the second display device indicating, e.g., "CALIBRATING DEVICE."

A seventh social cue proxy is an indication that the SGD is idle. This social cue proxy is advantageous in that it allows the conversation partner to know that the SGD is functioning properly, and that the user of the SGD device is not providing any other social cue proxy (e.g., the user is not typing a message or requesting assistance). In this example, the processor or software of the SGD may determine that the device is idle based on a lack of activity for a predefined time period (e.g., at least 5 seconds, at least 10 seconds, at least 15 seconds, at least 30 seconds, at least 1 minute). The indicator on the second display device may be a unique color indicating the SGD is idle, flashing lights or series of light movements, or a message on a screen of the second display device indicating, e.g., "IDLE."

An eighth social cue proxy is an indication that the SGD user's eyes are closed (e.g., sleeping). This social cue proxy may be determined using the eye gaze tracking device or a camera attached to or part of the SGD, wherein the eye gaze tracking device or camera monitors eye movement of the user and may determine if the user's eye lids are closed for at least a period of time. This is advantageous in that it allows the conversation partner to know that the SGD user is not paying attention or has fallen asleep. In this example, the processor or software of the SGD may determine that the SGD user's eye lids are closed (e.g., and the user is sleeping) based on monitoring of closed eyes for a predefined time period (e.g., at least 15 seconds, at least 30 seconds, at least 1 minute, at least 5 minutes). The indicator on the second display device may be a unique color indicating the SGD user is sleeping, flashing lights or series of light movements, or a message on a screen of the second display device indicating, e.g., "SLEEPING."

Additional social cue proxy examples are also possible, and may be programmed into the SGD software based on a user's particular communication preferences.

Emotional Proxies

In addition to, or in the alternative to social cue proxies, the user of the speech generating device may display a proxy for the user's emotion on the second display device of the SGD or communication system. The emotional proxy may be selected by the user or inferred through an analysis of the user's generated communication.

In certain examples, the user may select from a chart or table of emotions displayed on the first display device when preparing a communication message. The chart or table of emotions may be retrieved from a database or software program of the SGD. For simplicity and ease of selection, the chart or table may include a limited number of emotions from which to choose. In some examples, the user may modify the chart of emotions within the database based on a preference for identifying certain emotions.

In other examples, when preparing a communication message, the user may select an emoji displayed on the first display device as a proxy for the user's emotions. For example, the user could select a smiley face emoji to represent happiness, a sad face emoji with a tear drop to express grief, an angry red face emoji to represent anger, and so on. Again, for simplicity and ease of selection, the list of emoji to choose from may be a limited number of options to display and select from a single screen.

In yet other examples, the user of the SGD may select an image, graphic, or avatar displayed on the first display device as a proxy for the user's emotions. For example, the user could select an image of someone yelling to express anger, an image of someone laughing to express happiness, an image of a rainstorm to express sadness, an image of a quiet beach to express calmness, and so on. The image or simple graphic may be selected from a limited number of options for simplicity and ease of selection.

Alternatively, instead of the user providing an emotional proxy, an emotion may be inferred from the user's prepared message. Software of the SGD device may analyze the user's message for key words or phrases that may be tied to certain emotions. For example, if the user's message says "I hate onions," the software may identify the word "hate" to connote anger. The SGD may then identify that an emotional proxy for anger could be displayed on the second display device.

Following input from the user or inference by the SGD, the emotional proxy may be displayed on the second display device. The emotional proxy may be displayed or portrayed by a unique color, image, graphic, emoji, avatar, or text description, for example.

In one example, the user's selected or inferred emotion is linked with a specific color or color pattern. For example, the user may select the emotion from a chart, emoji, image, graphic, or avatar on the first display device, and the second display device display the emotional proxy in the form of a unique color. Shades of red may represent passion or anger; shades of orange may represent warmth or joyfulness; shades of yellow may represent energy or happiness; shades of green may represent peace or trust; shades of cyan may represent calmness or sadness; shades of magenta may represent boredom or disgust. If the second display device is an array of lighting elements (e.g., LEDs), the LEDs are illuminated with the identified color. If the second display device includes a display screen, the display screen or portion thereof is illuminated with the identified color. In certain examples, the intensity of the color goes up and down as the user's message is played (e.g., wherein the intensity of the lights flows with the words being spoken through the speakers). The identified color may remain displayed on the second display device until cleared by the user or until a predefined time has expired.

In additional examples, the user's selected or inferred emotion is linked with an emoji, image, graphic, or avatar. For example, after the user has selected the emotion on the first display device or the emotion has been inferred, the second display device may display the emotional proxy in the form of a unique emoji, image, graphic, or avatar. If the second display device is an array of lighting elements (e.g., LEDs), the LEDs may be illuminated in the form of an emoji or graphic such as a smiley face or a wink. If the second display device includes a display screen, the display screen or portion thereof may display the emoji, image, graphic, or avatar. The identified emotional proxy may remain displayed on the second display device until cleared by the user or until a predefined time has expired.

Exemplary Methods

Figure 9:
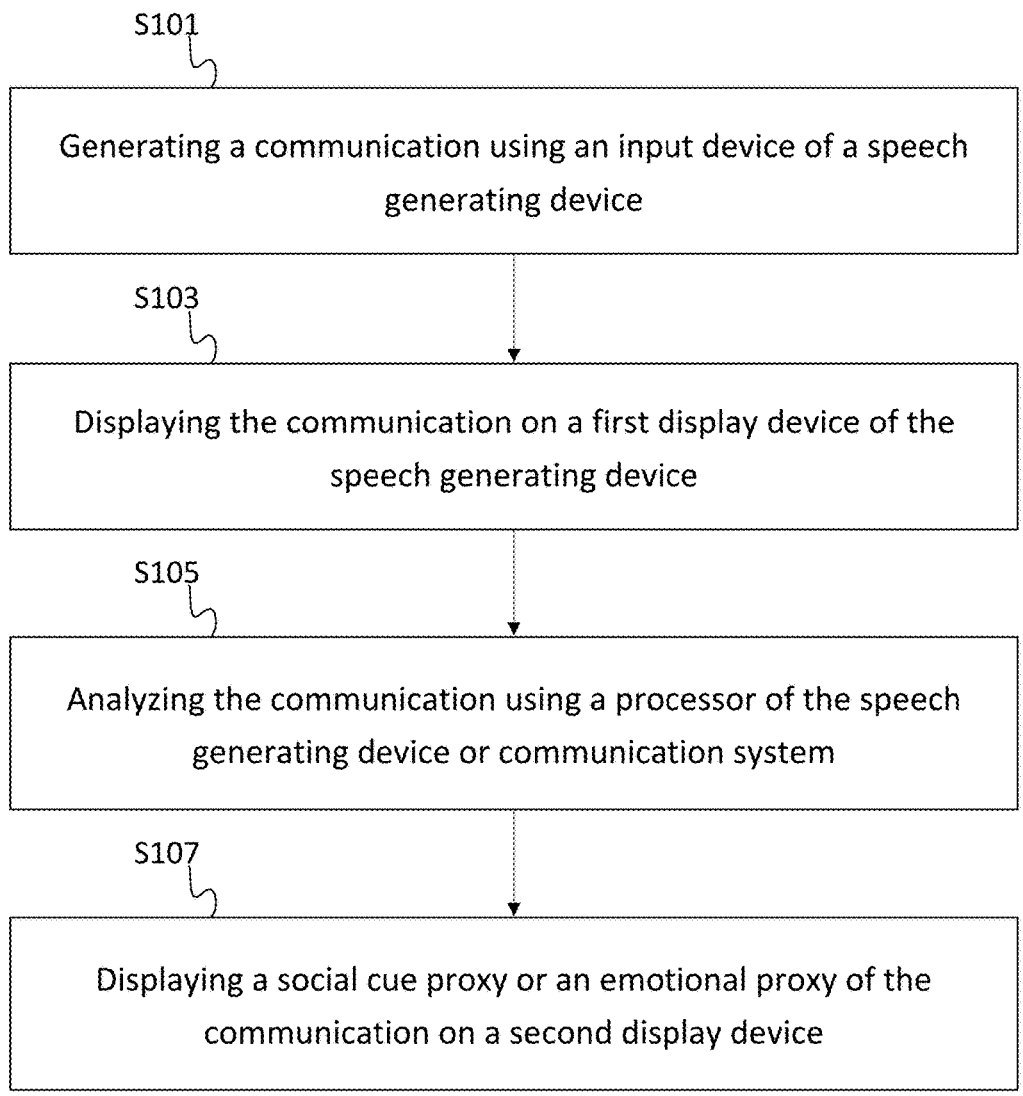
FIG. 9 is a flow diagram of a method of communicating using a speech generating device in accordance with a first example.

FIG. 9 depicts an exemplary method 900 for communicating using a speech generating device. At act S101, a communication is generated using an input device of the SGD. The input device may be an eye gaze tracking device. In certain examples, the user of the SGD may select images, emoji, or graphics displayed on the first display device to identify a social cue or emotion.

At act S103, the communication is displayed on the first display device of the SGD.

At act S105, the communication is analyzed by a processor of the SGD or communication system. The analysis may include inferring emotion from text generated by the user or from selected emotion imagery, emoji, or graphics selected by the user.

At act S107, a social cue proxy or an emotional proxy of the communication is displayed on a second display device of the communication system. In some examples, the second display device is part of and physically connected to the SGD. In other examples, the second display device is remote from and wirelessly in communication with the SGD.

In certain examples, an emotion is identified by the processor in the analyzing act, and the identified emotion is displayed on the second display device as the emotional proxy. In other examples, a social cue is identified by the processor in the analyzing act, and the identified social cue is displayed on the second display device as the social cue proxy.

Figure 10:
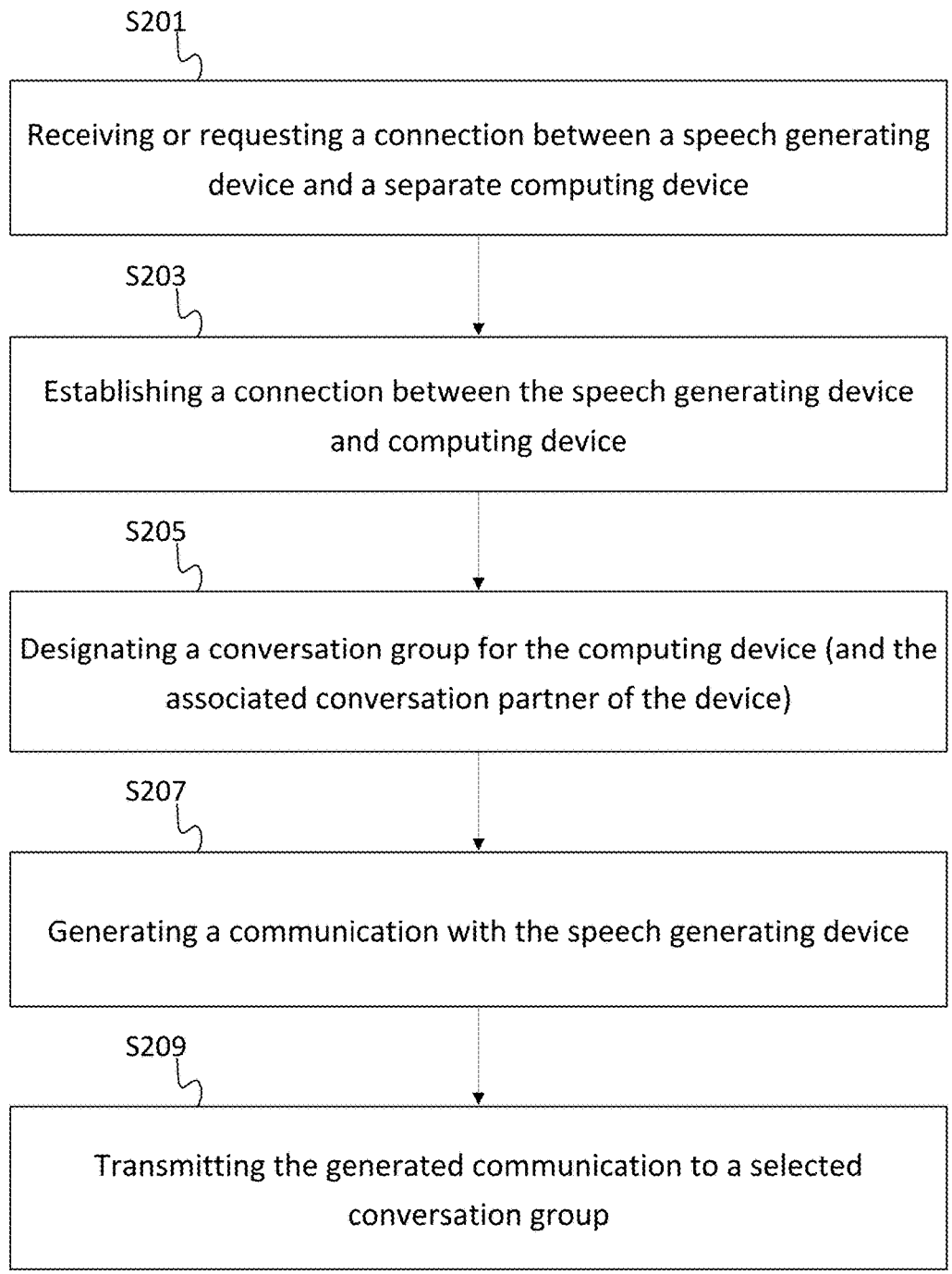
FIG. 10 is a flow diagram of a method of communicating using a speech generating device in accordance with a second example.

FIG. 10 depicts an exemplary method 1000 for communicating using a speech generating device. At act S201, a SGD receives a request to connect with a computing device of a potential conversation partner. This process may include installing a compatible software application on the computing device (e.g., mobile phone, tablet, laptop computer) and, through the application, making the request to connect with the software application of the SGD over a wireless communication network (e.g., via a server). Alternatively, in some examples, the SGD may make the request to connect the device with the computing device of the potential conversation partner.

At act S203, a connection is established between the speech generating device and the computing device. In some examples, the SGD user approves the conversation partner's request to connect. In alternative examples, the conversation partner approves the user's request to connect.

At act S205, the SGD user designates a conversation group for the computing device (and the associated conversation partner of the computing device). The conversation group may be a relationship category or social circle in which to place the conversation partner. This may include selecting a relationship category or social circle such as "Family," "Friends," "Work," "Medical," "Other," or any additional category the SGD user may create with their SGD. In some examples, the SGD user may also define a level of sharing for each conversation group for real-time updates of generated messages. In additional examples, the SGD user may define a level of sharing for each conversation group for historic or previous generated messages.

At act S207, the SGD user may generate a message with the SGD. The message or communication may be generated with an input device of the SGD. As noted above, the input device may be an eye gaze tracking device.

At act S209, the SGD user may transmit the generated message to a selected conversation group via a communication network, and any conversation partners and computing devices designated as part of the group. In some examples, the transmission is to all of the devices within the group that are currently connected over the communication network with the SGD. In certain examples, the computing devices not currently connected may receive a transmission when the device becomes connected at a later time.

Figure 11:
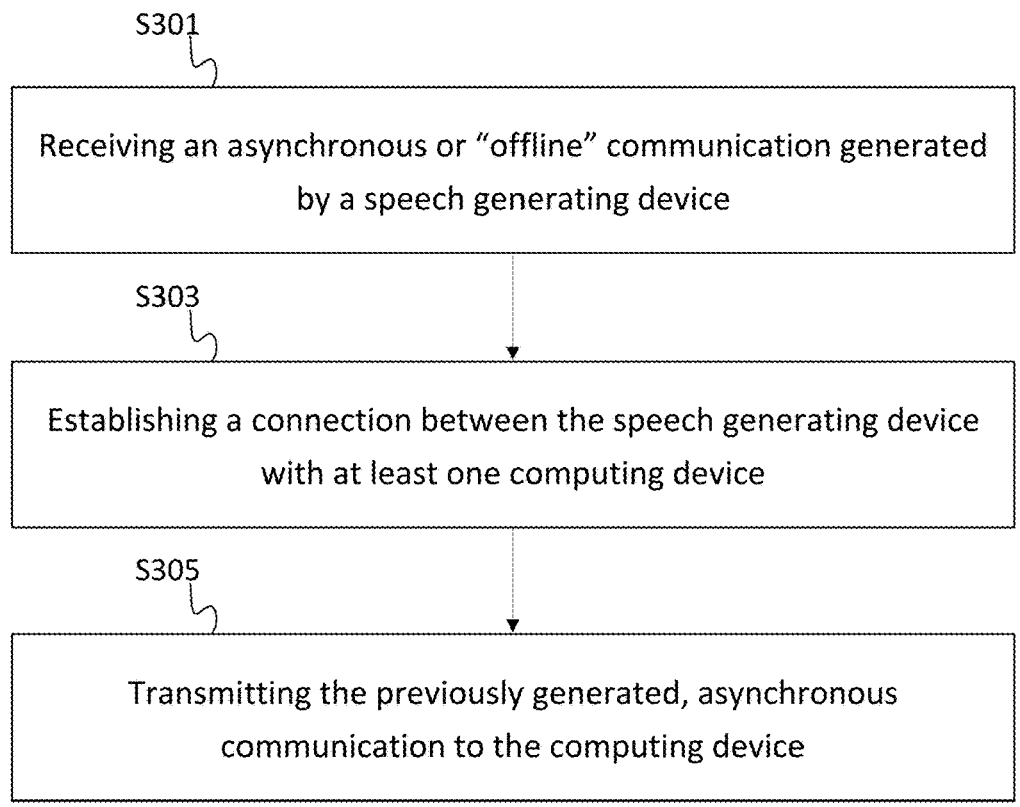
FIG. 11 is a flow diagram of a method of communicating using a speech generating device in accordance with a third example.

FIG. 11 depicts an exemplary method 1100 for communicating using a speech generating device. At act S301, a SGD user composes or generates an asynchronous or "offline" communication. The generated communication may be transmitted to and received by a server within the communication network. In certain examples, as previously discussed, the generated asynchronous message may include (1) communication preferences of the SGD user, (2) a pre-composed block of text to initiate a conversation on a particular subject, (3) multimedia, or (4) activity data.

At act S303, the speech generating device (with SGD user) connects with at least one computing device (with associated conversation partner). The connection may be made established by a server over a wireless communication network, wherein a software application of the SGD and a compatible software application of the computing device are connected. In some examples, the computing device is a mobile phone (e.g. smartphone), tablet, or laptop computer.

At act S305, at the time the connection is made or after the connection is made, the communication is transmitted from the SGD or the server to the computing device via communication network. In some examples, the SGD user initiates the transmission. In other examples, the server initiates the transmission when the server identifies the connection, or at a period of time after the identification of the connection.

Exemplary Computing Environment

Figure 12:
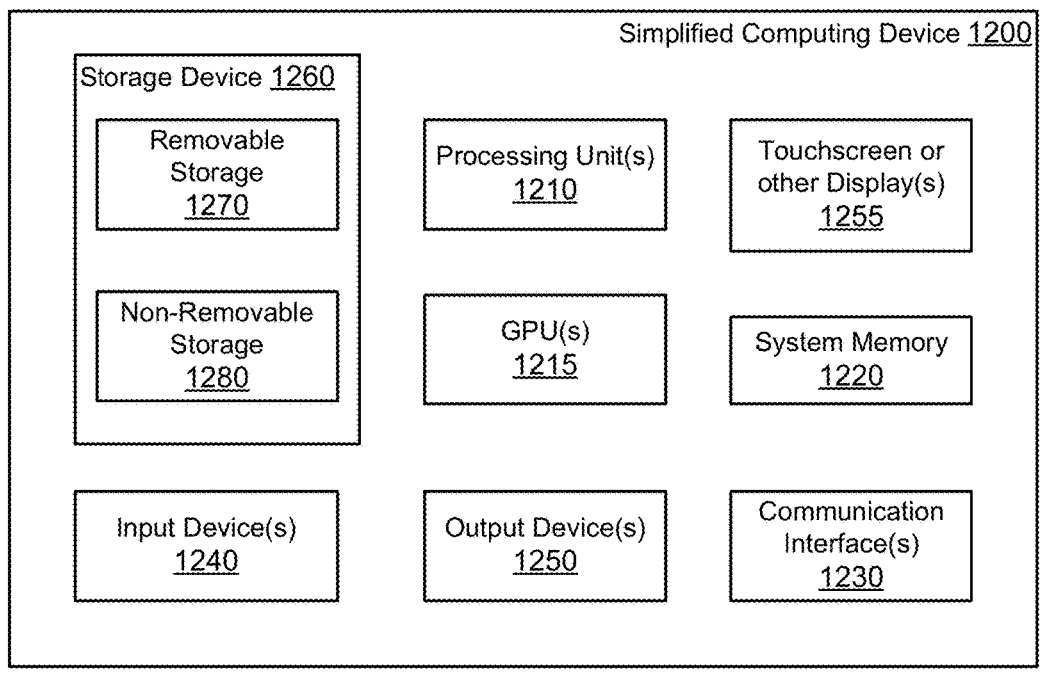
FIG. 12 is a block diagram of a computing environment in accordance with one example for implementation of the disclosed methods, one or more SGDs, or communication systems.

With reference to FIG. 12, the speech generating device, separate computing device, server, and/or communication system, as described above, may be an exemplary computing environment 1200 or incorporated within the exemplary computing environment. The computing environment 1200 may correspond with one of a wide variety of computing devices, including, but not limited to, personal computers (PCs), server computers, tablet and other handheld computing devices, laptop or mobile computers, communications devices such as mobile phones, multiprocessor systems, microprocessor-based systems, set top boxes, programmable consumer electronics, network PCs, minicomputers, mainframe computers, or audio or video media players.

The computing environment 1200 has sufficient computational capability and system memory to enable basic computational operations. In this example, the computing environment 1200 includes one or more processing unit(s) 1210, which may be individually or collectively referred to herein as a processor. The computing environment 1200 may also include one or more graphics processing units (GPUs) 1215. The processor 1210 and/or the GPU 1215 may include integrated memory and/or be in communication with system memory 1220. The processor 1210 and/or the GPU 1215 may be a specialized microprocessor, such as a digital signal processor (DSP), a very long instruction word (VLIW) processor, or other microcontroller, or may be a general purpose central processing unit (CPU) having one or more processing cores. The processor 1210, the GPU 1215, the system memory 1220, and/or any other components of the computing environment 1200 may be packaged or otherwise integrated as a system on a chip (SoC), application-specific integrated circuit (ASIC), or other integrated circuit or system.

The computing environment 1200 may also include other components, such as, for example, a communications interface 1230. One or more input devices 1240 (e.g., eye gaze tracking device; cameras; pointing devices such as a stylus, mouse, or joystick; keyboards; audio input devices; video input devices; haptic input devices; or devices for receiving wired or wireless data transmissions) may be provided. The input devices 1240 may include one or more touch-sensitive surfaces, such as track pads. Various output devices 1250, including touchscreen or touch-sensitive display(s) 1255, may also be provided. The output devices 1250 may include a variety of different audio output devices, video output devices, and/or devices for transmitting wired or wireless data transmissions. The output devices 1250 may also include one or more speakers for playing a generated message with the speech generating device.

The computing environment 1200 may also include a variety of computer readable media for storage of information such as computer-readable or computer-executable instructions, data structures, program modules, or other data. Computer readable media may be any available media accessible via storage devices 1260 and includes both volatile and nonvolatile media, whether in removable storage 1270 and/or non-removable storage 1280. Computer readable media may include computer storage media and communication media. Computer storage media may include both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may accessed by the processing units of the computing environment 1200.

In the above described examples, the communication network may include wired networks, wireless networks, or combinations thereof. The communication network may include a server configured to receive and transmit signals from the computing devices and speech generating devices. The wireless network may be a cellular telephone network, an 802.11, 802.16, 802.20, or WiMax network. Further, the network may be a public network, such as the Internet, a private network, such as an intranet, or combinations thereof, and may utilize a variety of networking protocols now available or later developed including, but not limited to TCP/IP based networking protocols.

While the computer-readable medium is described to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting example, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative example, dedicated hardware implementations, such as application specific integrated circuits, programmable logic arrays and other hardware devices, may be constructed to implement one or more of the examples described herein. Applications that may include the apparatus and systems of various examples can broadly include a variety of electronic and computer systems. One or more examples described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various examples of the present disclosure, the methods described herein may be implemented by software programs executable by a computer system. Further, in certain examples, implementations may include distributed processing, component/object distributed processing, and parallel processing. Alternatively, virtual computer system processing can be constructed to implement one or more of the methods or functionality as described herein.

Although the present specification describes components and functions that may be implemented in particular examples with reference to particular standards and protocols, the invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatuses can also be implemented as, special purpose logic circuitry, e.g., an FPGA (field programmable gate array) or an ASIC (application specific integrated circuit).

As used in this application, the term "circuitry" or "circuit" refers to all of the following: (a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in server, a cellular network device, or other network device.

Processors suitable for the execution of a computer program include, by way of example, both general and special purpose microprocessors, and any one or more processors of any kind of digital computer. Generally, a processor receives instructions and data from a read only memory or a random access memory or both. The essential elements of a computer are a processor for performing instructions and one or more memory devices for storing instructions and data. Generally, a computer also includes, or is operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., E PROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, examples of the subject matter described in this specification can be implemented on a device having a display, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Examples of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While the present claim scope has been described with reference to specific examples, which are intended to be illustrative only and not to be limiting of the claim scope, it will be apparent to those of ordinary skill in the art that changes, additions and/or deletions may be made to the disclosed embodiments without departing from the spirit and scope of the claims.

The foregoing description is given for clearness of understanding only, and no unnecessary limitations should be understood therefrom, as modifications within the scope of the claims may be apparent to those having ordinary skill in the art.

Claim Support Section

In a first embodiment, a communication system comprises a server configured to wirelessly communicate with a speech generating device and a computing device over a communication network, wherein the server is configured to: receive a generated communication from the speech generating device, establish a connection between the speech generating device and the computing device subsequent to receipt of the generated communication, and transmit the generated communication to the computing device.

In a second embodiment, with reference to the first embodiment, the speech generating device comprises a display device and an input device configured to generate the communication to be displayed on the display device.

In a third embodiment, with reference to the first or second embodiment, the generated communication is selected from the group consisting of: a communication preference, a pre-composed block of text, multimedia, an activity log, and a combination thereof.

In a fourth embodiment, with reference to the third embodiment, the communication preference is a request: (1) to ask only yes or no questions, (2) to view or not view over a shoulder of a user of the speech generating device as the user is composing a message, (3) to not finish a user's thought as the user is composing the message, or (4) to assist the user in completing or correcting the message using a computing device connected to the speech generating device.

In a fifth embodiment, with reference to the third or fourth embodiment, the multimedia comprises an image or video captured by the speech generating device.

In a sixth embodiment, with reference to any of embodiments 3-5, the activity log comprises an internet browsing history, a television or movie viewing history, a book reading or listening history, a music listening history, an article reading history, or an application usage history of a user of the speech generating device for a defined period of time.

In a seventh embodiment, with reference to any of embodiments 1-6, the server is configured to transmit the communication to the computing device based on whether the computing device is categorized in a specific conversation group.

In an eighth embodiment, a computing device comprises at least one processor, and at least one memory coupled to the at least one processor, the at least one memory including computer program code for one or more programs; the at least one memory and the computer program code configured to, with the at least one processor, cause the computing device to: establish a connection with a speech generating device via a communication network; and receive a transmission generated by the speech generating device, wherein the transmission comprises at least one of: (1) a previously generated communication, (2) a segment of a communication being generated in real-time, (3) a social cue proxy of the real-time communication, or (4) an emotional proxy of the previously generated communication or the real-time communication.

In a ninth embodiment, with reference to the eighth embodiment, the computing device is a personal computer, tablet computer, laptop computer, mobile phone, or wearable electronic device.

In a tenth embodiment, with reference to the eighth or ninth embodiment, the previously generated communication is a communication preference, a pre-composed block of text, multimedia, an activity log, or a combination thereof.

In an eleventh embodiment, with reference to any of embodiments 8-10, the segment of the real-time communication is a predefined segment length, the predefined segment length being a character, word, phrase, sentence, or block of text, and wherein the predefined segment length is based on a relationship between a user of the speech generating device and a conversation partner of the computing device.

In a twelfth embodiment, with reference to the eleventh embodiment, the at least one memory and the computer program code are further configured to cause the computing device to: assist the user of the speech generating device in generation of the real-time communication through a submission of (1) one or more corrections to words, phrases or sentences in the received transmission, and/or (2) one or more suggestions of a next word, phrase, or sentence.

In a thirteenth embodiment, with reference to any of embodiments 8-12, the social cue proxy is (1) an indication that a user of the speech generating device is typing or composing a message, (2) an indication that the user is speaking or about to speak, (3) an indication that the user is requesting to speak, (4) a request for assistance, (5) an identification of an emergency, (6) an indication that the user is calibrating an input device of the speech generating device, (7) an indication that the speech generating device is idle, or (8) an indication that the user is sleeping.

In a fourteenth embodiment, with reference to any of embodiments 8-13, the emotional proxy or the social cue proxy is displayed as a color or an arrangement of lights on a display screen of the computing device, the color or the arrangement of lights configured to identify an emotion or social cue.

In a fifteenth embodiment, a speech generating device comprises a display device, an input device configured to generate a communication to be displayed on the display device, and at least one processor coupled to the display device and input device, wherein the speech generating device, with the at least one processor, is configured to: establish a connection with one or more computing devices via a communication network, receive one or more suggestions from at least one computing device during generation of the communication; and display at least one suggestion on the display device as a shortcut input key.

In a sixteenth embodiment, with reference to the fifteenth embodiment, the speech generating device, with the at least one processor, is further configured to: define a relationship between a user of the speech generating device and a conversation partner of the computing device; and determine which of the one or more suggestions to display on the display screen based on the defined relationship.

In a seventeenth embodiment, with reference to the fifteenth or sixteenth embodiment, the speech generating device, with the at least one processor, is further configured to: define a relationship between a user of the speech generating device and a conversation partner of the computing device; identify a geographic location of the speech generating device; and determine which of the one or more suggestions to display on the display screen based on the defined relationship and the geographic location.

In an eighteenth embodiment, with reference to any of embodiments 15-17, the speech generating device, with the at least one processor, is further configured to: provide text predictions on the display screen as additional shortcut input keys, wherein the at least one suggestion is identified on the display screen in a different font, color, or shortcut input key size as the additional shortcut input keys.

In a nineteenth embodiment, with reference to the eighteenth embodiment, the at least one suggestion is identified in the different font, color, or shortcut input key size based on a relationship between a user of the speech generating device and a conversation partner of the computing device.

In a twentieth embodiment, with reference to any of embodiments 15-19, the speech generating device, with the at least one processor, is further configured to: provide text predictions on the display screen as additional shortcut input keys, wherein the at least one suggestion is identified on the display screen in a same font, color, and shortcut input key size as the additional shortcut input keys.

What is claimed is:

1. A communication system for relaying asynchronous communications between a user of a speech generating device and a conversation partner of a computing device during a synchronous conversation, the communication system comprising:
a server configured to wirelessly communicate with the speech generating device and the computing device over a communication network, wherein the server is configured to:
receive a generated communication for asynchronous communication composed by the user of the speech generating device prior to establishing a connection between the speech generating device and the computing device;
establish the connection between the speech generating device and the computing device subsequent to receipt of the generated communication;
facilitate an exchange of one or more messages between the speech generating device of the user and the computing device of the conversation partner as part of the synchronous conversation;
transmit the generated communication to the computing device, the generated communication including content that is shared with the conversation partner to fill a conversational gap occurring from a low throughput of communication as part of the synchronous conversation by the user;

receive, via the speech generating device, additional speech constructed by the user for the synchronous conversation during presentation of the generated communication to the conversation partner at the computing device; and transmit the additional speech to the computing device for presentation to the conversation partner.

2. The communication system of claim 1, wherein the speech generating device comprises a display device and an input device configured to generate the communication to be displayed on the display device.

3. The communication system of claim 1, wherein the generated communication is selected from the group consisting of: a communication preference, a pre-composed block of text, multimedia, an activity log, and a combination thereof.

4. The communication system of claim 3, wherein the multimedia comprises an image or video captured by the speech generating device.

5. The communication system of claim 3, wherein the activity log comprises an internet browsing history, a television or movie viewing history, a book reading or listening history, a music listening history, an article reading history, or an application usage history of the user of the speech generating device for a defined period of time.

6. The communication system of claim 1, wherein the generated communication is a communication preference requesting the conversation partner of the computing device to ask only yes or no questions to the user of the speech generating device.

7. The communication system of claim 1, wherein the server is configured to transmit the communication to the computing device based on whether the computing device is categorized in a specific conversation group.

8. The communication system of claim 1, wherein the generated communication is a communication preference requesting the conversation partner of the computing device to view or not view over a shoulder of the user of the speech generating device as the user of the speech generating device is composing one of the one or more messages.

9. The communication system of claim 1, wherein the generated communication is a communication preference requesting the conversation partner of the computing device to not finish a thought of the user of the speech generating device as the user of the speech generating device is composing one of the one or more messages.

10. The communication system of claim 1, wherein the generated communication is a communication preference requesting the conversation partner of the computing device to assist the user of the speech generating device in completing or correcting one of the one or more messages using the computing device connected to the speech generating device.

11. A computing device comprising:
a display screen;
at least one processor; and
at least one memory coupled to the at least one processor, the at least one memory including computer program code for one or more programs; the at least one memory and the computer program code configured to, with the at least one processor, cause the computing device to:
establish a connection with a speech generating device via a communication network for a synchronous conversation between a user of the speech generating device and a conversation partner of the computing device;
receive a transmission generated by the speech generating device for asynchronous communication composed by the user of the speech generating device prior to establishing the connection between the speech generating device and the computing device;
facilitate an exchange of one or more messages between the speech generating device of the user and the computing device of the conversation partner as part of the synchronous conversation;
display the transmission on the display screen, the transmission including content that is shared with the conversation partner to fill a conversational gap occurring from a low throughput of communication as part of the synchronous conversation by the user;
receive, via the speech generating device, additional speech constructed by the user for the synchronous conversation during display of the transmission to the conversation partner at the computing device; and
display the additional speech to the conversation partner,
wherein the transmission comprises a previously generated communication composed by the user of the speech generating device.

12. The computing device of claim 11, wherein the computing device is a personal computer, tablet computer, laptop computer, mobile phone, or wearable electronic device.

13. The computing device of claim 11, wherein the previously generated communication is a communication preference defining how to interact with the user of the speech generating device.

14. The computing device of claim 11, wherein the at least one memory and the computer program code are further configured to cause the computing device to:
assist the user of the speech generating device in generation of a real-time communication through a submission of (1) one or more corrections to words, phrases or sentences in the received transmission, and/or (2) one or more suggestions of a next word, phrase, or sentence.

15. The computing device of claim 11, wherein the previously generated communication is a pre-composed block of text.

16. The computing device of claim 11, wherein the previously generated communication is a multimedia.

17. The computing device of claim 11, wherein the previously generated communication is an activity log of the user of the speech generating device.

* * * * *